United States Patent
Raffle et al.

(10) Patent No.: US 9,870,049 B2
(45) Date of Patent: Jan. 16, 2018

(54) REFLECTIVE LENSES TO AUTO-CALIBRATE A WEARABLE SYSTEM

(71) Applicant: Google LLC, Mountain View, CA (US)

(72) Inventors: Hayes Solos Raffle, Palo Alto, CA (US); Simon Robert Prakash, Los Gatos, CA (US)

(73) Assignee: Google LLC, Mountain View, CA (US)

(*) Notice: Subject to any disclaimer, the term of this patent is extended or adjusted under 35 U.S.C. 154(b) by 303 days.

(21) Appl. No.: 14/814,920

(22) Filed: Jul. 31, 2015

(65) Prior Publication Data

US 2017/0031435 A1     Feb. 2, 2017

(51) Int. Cl.

| | |
|---|---|
| *G06F 3/01* | (2006.01) |
| *G06K 9/00* | (2006.01) |
| *G02B 27/01* | (2006.01) |
| *G06K 19/06* | (2006.01) |
| *G02C 7/02* | (2006.01) |
| *G02B 27/02* | (2006.01) |
| *G06K 9/46* | (2006.01) |
| *A61B 3/113* | (2006.01) |
| *G02B 19/00* | (2006.01) |
| *H04L 9/32* | (2006.01) |

(Continued)

(52) U.S. Cl.
CPC ............ *G06F 3/013* (2013.01); *G02B 27/017* (2013.01); *G02B 27/0172* (2013.01); *G06K 9/00604* (2013.01); *A61B 3/113* (2013.01); *G02B 19/009* (2013.01); *G02B 27/01* (2013.01); *G02B 27/02* (2013.01); *G02B 2027/014* (2013.01);

(Continued)

(58) Field of Classification Search
CPC ....... G06F 3/013; G02B 19/009; G02B 27/01; G02B 27/02; G02B 27/017; G02B 27/0172; G02B 2027/0138; G02B 2027/014; G02B 2027/0178; G02B 2027/0187; G06K 9/00604; G06K 9/4661; G06K 19/0614; G02C 7/021; G06T 2207/10048; H04L 9/32; A61B 3/113

See application file for complete search history.

(56) References Cited

U.S. PATENT DOCUMENTS 8,384,774 B2    2/2013 Gallagher
8,699,089 B2 *  4/2014 Eschbach ........... H04N 1/32261
                                                              358/1.9

(Continued)

FOREIGN PATENT DOCUMENTS

KR    20140090968    7/2014

OTHER PUBLICATIONS

International Searching Authority, International Search Report and Written Opinion dated Nov. 3, 2016, issued in connection with International Patent Application No. PCT/US2016/044565, filed on Jul. 28, 2016, 9 pages.

*Primary Examiner* — Jwalant Amin
(74) *Attorney, Agent, or Firm* — McDonnell Boehnen Hulbert & Berghoff LLP

(57) ABSTRACT

Example embodiments include a lens having an IR-reflective coating that is selectively applied to form a variable infrared (IR) interaction pattern on the lens. The variable IR interaction pattern may vary in the manner it interacts with IR wavelengths, so as to provide a machine-readable code when the lens is illuminated by IR light. Accordingly, variable IR interaction patterns may be used to identify particular lenses. Accordingly, a glasses-style, modular, head-mountable device (HMD) may identify which of a number of different possible lenses are currently attached to the HMD, and update certain processes according to the lens or lenses is or are attached. For example, an HMD may calibrate an eye-tracking process according to the particular lens that is attached.

20 Claims, 15 Drawing Sheets

(52) U.S. Cl.
CPC ............ *G02B 2027/0138* (2013.01); *G02B 2027/0178* (2013.01); *G02B 2027/0187* (2013.01); *G02C 7/021* (2013.01); *G06K 9/4661* (2013.01); *G06K 19/0614* (2013.01); *G06T 2207/10048* (2013.01); *H04L 9/32* (2013.01)

(56) References Cited

U.S. PATENT DOCUMENTS

| | | | |
|---|---|---|---|
| 8,942,419 B1* | 1/2015 | Wu | G01S 17/06 382/103 |
| 8,971,570 B1 | 3/2015 | Raffle et al. | |
| 2012/0128330 A1* | 5/2012 | Mahdavi | G06K 9/2018 386/252 |
| 2012/0319016 A1* | 12/2012 | Kuhlman | F24C 7/04 250/505.1 |
| 2013/0002932 A1 | 1/2013 | Guenter et al. | |
| 2013/0114850 A1* | 5/2013 | Publicover | G06K 9/00604 382/103 |
| 2013/0163089 A1* | 6/2013 | Bohn | G02B 27/0172 359/630 |
| 2014/0337634 A1 | 11/2014 | Starner et al. | |
| 2015/0014417 A1 | 1/2015 | Finlow-Bats et al. | |
| 2015/0062533 A1* | 3/2015 | Toner | G02C 7/049 351/209 |
| 2015/0098620 A1* | 4/2015 | Wu | G01S 17/06 382/103 |
| 2015/0212326 A1 | 7/2015 | Kress et al. | |
| 2016/0008718 A1* | 1/2016 | Schaerer | A63F 13/213 463/34 |
| 2017/0038834 A1* | 2/2017 | Wilson | G02B 27/02 |

* cited by examiner

REFLECTIVE LENSES TO AUTO-CALIBRATE A WEARABLE SYSTEM

BACKGROUND

Unless otherwise indicated herein, the materials described in this section are not prior art to the claims in this application and are not admitted to be prior art by inclusion in this section.

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, and/or less obtrusive.

The trend toward miniaturization of computing hardware, peripherals, as well as of sensors, detectors, and image and audio processors, among other technologies, has helped open up a field sometimes referred to as "wearable computing." In the area of image and visual processing and production, in particular, it has become possible to consider wearable displays that place a graphic display close enough to a wearer's (or user's) eye(s) such that the displayed image appears as a normal-sized image, such as might be displayed on a traditional image display device. The relevant technology may be referred to as "near-eye displays."

Wearable computing devices with near-eye displays may also be referred to as "head-mountable displays" (HMDs), "head-mounted displays," "head-mounted devices," or "head-mountable devices." A head-mountable display places a graphic display or displays close to one or both eyes of a wearer. To generate the images on a display, a computer processing system may be used. Such displays may occupy a wearer's entire field of view, or only occupy part of wearer's field of view. Further, head-mounted displays may vary in size, taking a smaller form such as a glasses-style display or a larger form such as a helmet, for example.

Emerging and anticipated uses of wearable displays include applications in which users interact in real time with an augmented or virtual reality. Such applications can be mission-critical or safety-critical, such as in a public safety or aviation setting. The applications can also be recreational, such as interactive gaming. Many other applications are also possible.

SUMMARY

In one aspect, an example method involves a computing system: (a) receiving infrared (IR) image data of an inner surface of a lens of a head-mountable device (HMD), wherein the image data is captured while the inner surface of the lens is illuminated with infrared light; (b) detecting, in the IR image data of the inner surface of the lens, a reflection of an eye area off of the inner surface of the lens; (c) detecting, in the IR image data of the inner surface of the lens, a machine-readable code resulting from a variable IR interaction pattern of the lens; (d) determining a lens that corresponds to the detected machine-readable code; (e) calibrating an eye-analysis process based on the determined lens; and (f) after calibrating the eye-analysis process, applying the eye-analysis process to the reflection of the eye area to determine data corresponding to the eye.

In another aspect, an example HMD includes: (i) a lens comprising an variable infrared (IR) interaction pattern that defines a machine-readable code; (ii) an IR light source arranged on a frame of the HMD to emit IR light towards the at least one lens; (iii) an IR camera arranged on a frame of the HMD and operable to capture IR image data while the at least one lens is illuminated by the IR light source; and (iv) an onboard computing system that is operable to: (a) detect, in the IR image data, a reflection of an eye area off of the inner surface of the lens; (b) detect, in the IR image data, the machine-readable code resulting from the variable IR interaction pattern on the lens; (c) determine a lens that corresponds to the detected machine-readable code; (d) calibrate an eye-analysis process based on the determined lens; and (e) apply the calibrated eye-analysis process to the reflection off of the eye area to determine data corresponding to the eye.

In yet another aspect, an example lens comprises an inner surface having an variable infrared (IR) interaction formed by a selectively applied optical coating. The variable IR interaction pattern defines a machine-readable code, which in turn identifies the optical lens.

These as well as other aspects, advantages, and alternatives will become apparent to those of ordinary skill in the art by reading the following detailed description, with reference where appropriate to the accompanying drawings.

DETAILED DESCRIPTION

Figure 1A:
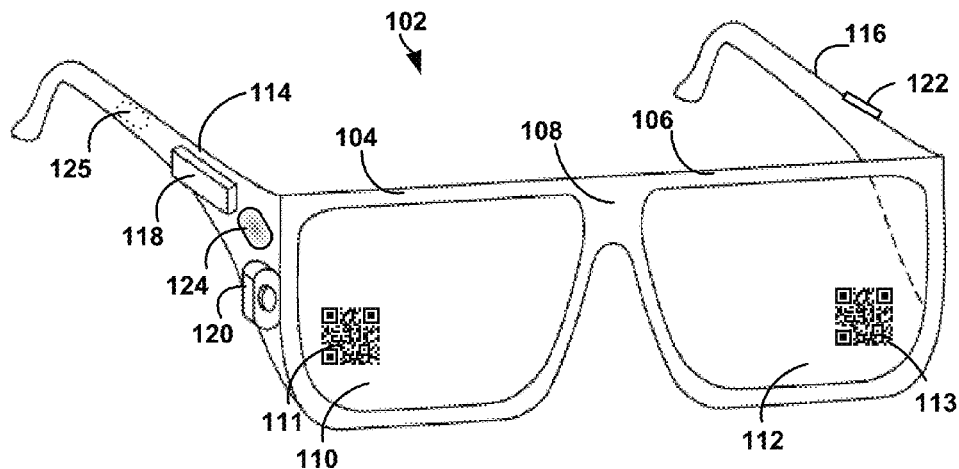
FIG. 1A illustrates a wearable computing system according to an example embodiment.

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

I. OVERVIEW

A glasses-style head-mountable device (HMD) may include various systems for determining the position of the wearer's eye and/or detecting winks and blinks. Such systems may allow the user to interact with their HMD using eye gestures. In some implementations, eye data may be obtained using a system that detects reflections of the eye area, which are reflected from an inner surface of the HMD's eyeglass lens. Such techniques are, in a sense, using the inner surface of the lens as a mirror to obtain image data of the eye. Provided with (i) a known or approximated arrangement of the camera, the eyeglass lens, and the eye, and (ii) certain optical characteristics of the eyeglass lens and camera lens, image data of a reflection of an eye area off of the lens may be used to determine, e.g., position and/or movement of the eye, and/or whether the eye is open or closed. Further, by analyzing a sequence of such reflected images, an eye tracking system can determine how the eye moves over time.

In another aspect, HMDs with modular frames and lenses are desirable, as they allow a user to swap out lens and frames for aesthetic reasons, and possibly for functional reasons as well (e.g., swapping in a frame with tinted lenses (i.e., sunglasses), or switching to frame with prescription lenses on a day when the wearer decides not to wear their contact lenses). However, switching to a different lens may reduce the accuracy of an eye tracking system that relies on a reflection of the eye from an eyeglass lens, since the system relies upon knowing certain characteristics of the lens (e.g., radius of curvature, pantoscopic tilt, and wrap). Accordingly, example embodiments may provide systems and methods that discretely and automatically detect when a frame with a different lens has been attached to an HMD, and responsively recalibrate an eye-tracking process based on the characteristics of the new lens.

Accordingly, example embodiments may provide a lens or lenses with a machine-readable pattern defined by a variable IR-interaction pattern formed by a selectively-applied lens coating. In particular, a coating having certain reflective or absorptive properties with respect to IR wavelengths may be applied to a surface of a lens in the shape of a machine-readable code. The coating may be such that the machine-readable code is not visible to the human eye (or is difficult to see from a straight-ahead viewing angle), but is visible in an image of the lens that is captured by an IR camera while the lens is illuminated by an IR light source.

In a further aspect, an HMD may include a detachable (e.g., modular) frame with at least one lens that is selectively coated with a variable IR-interaction pattern that defines a machine readable code (e.g., a bar code or QR code). Further, since the machine readable code may identify the lens (or at least the particular type or model of lens), the HMD may include an IR light source and IR camera that are arranged to detect the machine-readable code and responsively recalibrate an eye-tracking process based on the characteristics of the lens identified by the machine-readable code.

Note that example lenses may have other applications beyond HMDs, and/or other purposes in the context of HMDs. For example, such IR machine-readable codes may provide anti-counterfeiting measures on any surface that can be coated in such a manner, including HMD lenses, since aftermarket lenses would need to duplicate both the authentic frame and lens shape and build, and the coating with the machine readable code.

II. EXAMPLE WEARABLE COMPUTING DEVICES

Systems and devices in which example embodiments may be implemented will now be described in greater detail. In general, an example system may be implemented in or may take the form of a wearable computer (also referred to as a wearable computing device). In an example embodiment, a wearable computer takes the form of or includes a head-mountable device (HMD).

An example system may also be implemented in or take the form of other devices, such as a mobile phone, among other possibilities. Further, an example system may take the form of non-transitory computer readable medium, which has program instructions stored thereon that are executable by at a processor to provide the functionality described herein. An example system may also take the form of a device such as a wearable computer or mobile phone, or a subsystem of such a device, which includes such a non-transitory computer readable medium having such program instructions stored thereon.

An HMD may generally be any display device that is capable of being worn on the head and places a display in front of one or both eyes of the wearer. An HMD may take various forms such as a helmet or eyeglasses. As such, references to "eyeglasses" or a "glasses-style" HMD should be understood to refer to an HMD that has a glasses-like frame so that it can be worn on the head. Further, example embodiments may be implemented by or in association with an HMD with a single display or with two displays, which may be referred to as a "monocular" HMD or a "binocular" HMD, respectively.

FIG. 1A illustrates a wearable computing system according to an example embodiment. In FIG. 1A, the wearable computing system takes the form of a head-mountable device (HMD) 102 (which may also be referred to as a head-mounted display). It should be understood, however, that example systems and devices may take the form of or be implemented within or in association with other types of devices, without departing from the scope of the invention. As illustrated in FIG. 1A, the HMD 102 includes frame elements including lens-frames 104, 106 and a center frame support 108, lens elements 110, 112, and extending side-arms 114, 116. The center frame support 108 and the extending side-arms 114, 116 are configured to secure the HMD 102 to a user's face via a user's nose and ears, respectively.

Each of the frame elements 104, 106, and 108 and the extending side-arms 114, 116 may be formed of a solid structure of plastic and/or metal, or may be formed of a hollow structure of similar material so as to allow wiring and component interconnects to be internally routed through the HMD 102. Other materials may be possible as well.

One or more of each of the lens elements 110, 112 may be formed of any material that can suitably display a projected image or graphic. Each of the lens elements 110, 112 may also be sufficiently transparent to allow a user to see through the lens element. Combining these two features of the lens elements may facilitate an augmented reality or heads-up display where the projected image or graphic is superimposed over a real-world view as perceived by the user through the lens elements.

The extending side-arms 114, 116 may each be projections that extend away from the lens-frames 104, 106, respectively, and may be positioned behind a user's ears to secure the HMD 102 to the user. The extending side-arms 114, 116 may further secure the HMD 102 to the user by extending around a rear portion of the user's head. Additionally or alternatively, for example, the HMD 102 may connect to or be affixed within a head-mounted helmet structure. Other configurations for an HMD are also possible.

The HMD 102 may also include an on-board computing system 118, an image capture device 120, a sensor 122, and a finger-operable touch pad 124. The on-board computing system 118 is shown to be positioned on the extending side-arm 114 of the HMD 102; however, the on-board computing system 118 may be provided on other parts of the HMD 102 or may be positioned remote from the HMD 102 (e.g., the on-board computing system 118 could be wire- or wirelessly-connected to the HMD 102). The on-board computing system 118 may include a processor and memory, for example. The on-board computing system 118 may be configured to receive and analyze data from the image capture device 120 and the finger-operable touch pad 124 (and possibly from other sensory devices, user interfaces, or both) and generate images for output by the lens elements 110 and 112.

The image capture device 120 may be, for example, a camera that is configured to capture still images and/or to capture video. In the illustrated configuration, image capture device 120 is positioned on the extending side-arm 114 of the HMD 102; however, the image capture device 120 may be provided on other parts of the HMD 102. The image capture device 120 may be configured to capture images at various resolutions or at different frame rates. Many image capture devices with a small form-factor, such as the cameras used in mobile phones or webcams, for example, may be incorporated into an example of the HMD 102.

Further, although FIG. 1A illustrates one image capture device 120, more image capture device may be used, and each may be configured to capture the same view, or to capture different views. For example, the image capture device 120 may be forward facing to capture at least a portion of the real-world view perceived by the user. This forward facing image captured by the image capture device 120 may then be used to generate an augmented reality where computer generated images appear to interact with or overlay the real-world view perceived by the user.

The sensor 122 is shown on the extending side-arm 116 of the HMD 102; however, the sensor 122 may be positioned on other parts of the HMD 102. For illustrative purposes, only one sensor 122 is shown. However, in an example embodiment, the HMD 102 may include multiple sensors. For example, an HMD 102 may include sensors 102 such as one or more gyroscopes, one or more accelerometers, one or more magnetometers, one or more light sensors, one or more infrared sensors, and/or one or more microphones. Other sensing devices may be included in addition or in the alternative to the sensors that are specifically identified herein.

The finger-operable touch pad 124 is shown on the extending side-arm 114 of the HMD 102. However, the finger-operable touch pad 124 may be positioned on other parts of the HMD 102. Also, more than one finger-operable touch pad may be present on the HMD 102. The finger-operable touch pad 124 may be used by a user to input commands. The finger-operable touch pad 124 may sense at least one of a pressure, position and/or a movement of one or more fingers via capacitive sensing, resistance sensing, or a surface acoustic wave process, among other possibilities. The finger-operable touch pad 124 may be capable of sensing movement of one or more fingers simultaneously, in addition to sensing movement in a direction parallel or planar to the pad surface, in a direction normal to the pad surface, or both, and may also be capable of sensing a level of pressure applied to the touch pad surface. In some embodiments, the finger-operable touch pad 124 may be formed of one or more translucent or transparent insulating layers and one or more translucent or transparent conducting layers. Edges of the finger-operable touch pad 124 may be formed to have a raised, indented, or roughened surface, so as to provide tactile feedback to a user when the user's finger reaches the edge, or other area, of the finger-operable touch pad 124. If more than one finger-operable touch pad is present, each finger-operable touch pad may be operated independently, and may provide a different function.

In a further aspect, HMD 102 may be configured to receive user input in various ways, in addition or in the alternative to user input received via finger-operable touch pad 124. For example, on-board computing system 118 may implement a speech-to-text process and utilize a syntax that maps certain spoken commands to certain actions. In addition, HMD 102 may include one or more microphones via which a wearer's speech may be captured. Configured as such, HMD 102 may be operable to detect spoken commands and carry out various computing functions that correspond to the spoken commands.

As another example, HMD 102 may interpret certain head-movements as user input. For example, when HMD 102 is worn, HMD 102 may use one or more gyroscopes and/or one or more accelerometers to detect head movement. The HMD 102 may then interpret certain head-movements as being user input, such as nodding, or looking up, down, left, or right. An HMD 102 could also pan or scroll through graphics in a display according to movement. Other types of actions may also be mapped to head movement.

As yet another example, HMD 102 may interpret certain gestures (e.g., by a wearer's hand or hands) as user input. For example, HMD 102 may capture hand movements by analyzing image data from image capture device 120, and initiate actions that are defined as corresponding to certain hand movements.

As a further example, HMD 102 may interpret eye movement as user input. In particular, HMD 102 may include one or more inward-facing image capture devices and/or one or more other inward-facing sensors (not shown) sense a user's eye movements and/or positioning. As such, certain eye movements may be mapped to certain actions. For example, certain actions may be defined as corresponding to movement of the eye in a certain direction, a blink, and/or a wink, among other possibilities.

HMD 102 also includes a speaker 125 for generating audio output. In one example, the speaker could be in the form of a bone conduction speaker, also referred to as a bone conduction transducer (BCT). Speaker 125 may be, for example, a vibration transducer or an electroacoustic transducer that produces sound in response to an electrical audio signal input. The frame of HMD 102 may be designed such that when a user wears HMD 102, the speaker 125 contacts the wearer. Alternatively, speaker 125 may be embedded within the frame of HMD 102 and positioned such that, when the HMD 102 is worn, speaker 125 vibrates a portion of the frame that contacts the wearer. In either case, HMD 102 may be configured to send an audio signal to speaker 125, so that vibration of the speaker may be directly or indirectly transferred to the bone structure of the wearer. When the vibrations travel through the bone structure to the bones in the middle ear of the wearer, the wearer can interpret the vibrations provided by BCT 125 as sounds.

Various types of bone-conduction transducers (BCTs) may be implemented, depending upon the particular implementation. Generally, any component that is arranged to vibrate the HMD 102 may be incorporated as a vibration transducer. Yet further it should be understood that an HMD 102 may include a single speaker 125 or multiple speakers. In addition, the location(s) of speaker(s) on the HMD may vary, depending upon the implementation. For example, a speaker may be located proximate to a wearer's temple (as shown), behind the wearer's ear, proximate to the wearer's nose, and/or at any other location where the speaker 125 can vibrate the wearer's bone structure.

Figure 1B:
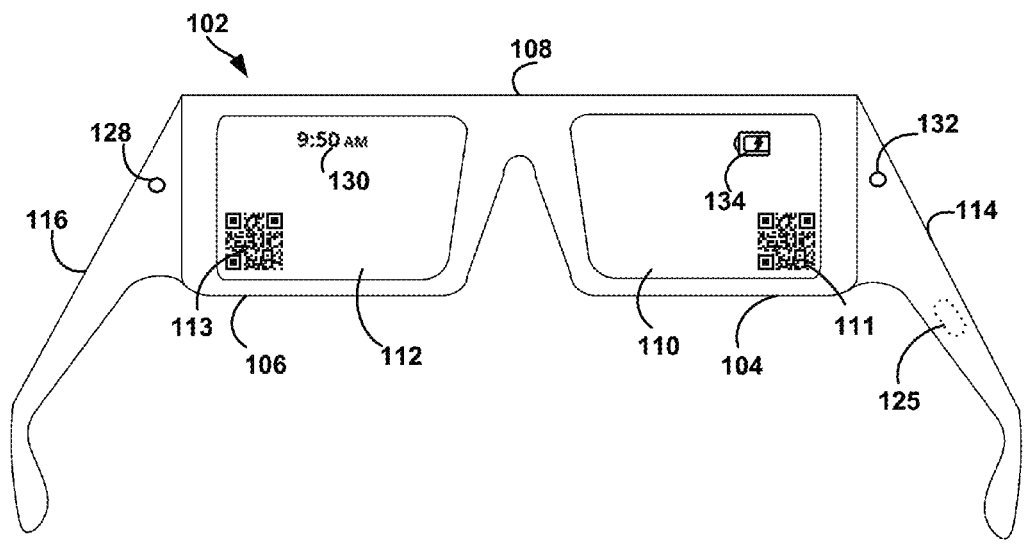
FIG. 1B illustrates an alternate view of the wearable computing device illustrated in FIG. 1A.

FIG. 1B illustrates an alternate view of the wearable computing device illustrated in FIG. 1A. As shown in FIG. 1B, the lens elements 110, 112 may act as display elements. The HMD 102 may include a first projector 128 coupled to an inside surface of the extending side-arm 116 and configured to project a display 130 onto an inside surface of the lens element 112. Additionally or alternatively, a second projector 132 may be coupled to an inside surface of the extending side-arm 114 and configured to project a display 134 onto an inside surface of the lens element 110.

The lens elements 110, 112 may act as a combiner in a light projection system and may include a coating that reflects the light projected onto them from the projectors 128, 132. In some embodiments, a reflective coating may not be used (e.g., when the projectors 128, 132 are scanning laser devices).

In alternative embodiments, other types of display elements may also be used. For example, the lens elements 110, 112 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 104, 106 for driving such a matrix display. Alternatively or additionally, a laser or LED source and scanning system could be used to draw a raster display directly onto the retina of one or more of the user's eyes. Other possibilities exist as well.

In a further aspect, lens elements 110, 112 could each be a coded lens. For example, in FIGS. 1A and 1B, each lens elements 110, 112 is shown as having a respective variable infrared ("IR") interaction pattern 111, 113. Each variable IR interaction 111, 113 may be formed by an optical coating, or a combination of optical coatings, on the respective lens. Such coating or coatings may be IR reflective, IR transmissive, and/or IR absorptive to varying degrees, and may be applied in a pattern to form the variable IR interaction pattern. Further, the variable IR interaction pattern may not be visible to the naked eye, and may only be noticeable when illuminated by IR radiation (e.g., from an IR light source) and/or viewed through an IR filter.

Further, each variable IR interaction pattern 111, 113 may serve to identify its respective lens. For instance, in FIGS. 1A and 1B, each variable IR interaction pattern 111, 113 is a QR code, which can identify the corresponding lens element 110, 112. Other types of coding can also be provided with a variable IR interaction pattern.

Note that in some embodiments, an HMD could include two lens elements, but only one lens element with such a variable IR interaction pattern. In such case, the single variable IR interaction pattern could identify one or both lenses (and possibly other components of the HMD that are coupled to the lens or lenses).

Further, note that such variable IR interaction patterns can be implemented on a lens that also serves as a graphic display; e.g., in an augmented reality or heads-up display where a projected image or graphic is superimposed over a real-world view as perceived by the user through the lens elements. However, a variable IR interaction pattern could also be implemented on a lens of an HMD that does not include a display; e.g., where the lens or lenses otherwise function in the same manner as lenses on traditional eyeglasses or sunglasses. For instance, an HMD might serve primarily as a device to support voice interaction, so that the user can engage in conversational interactions using microphone(s), speaker(s), and an onboard computing system integrated in a glasses-style HMD. Such an HMD may be a dedicated voice interaction device, and thus may not include any type of camera or graphic display. Such an HMD could also tether to a user's mobile phone or other computing devices with displays, so that non-voice related feedback and input would be possible.

Figure 1C:
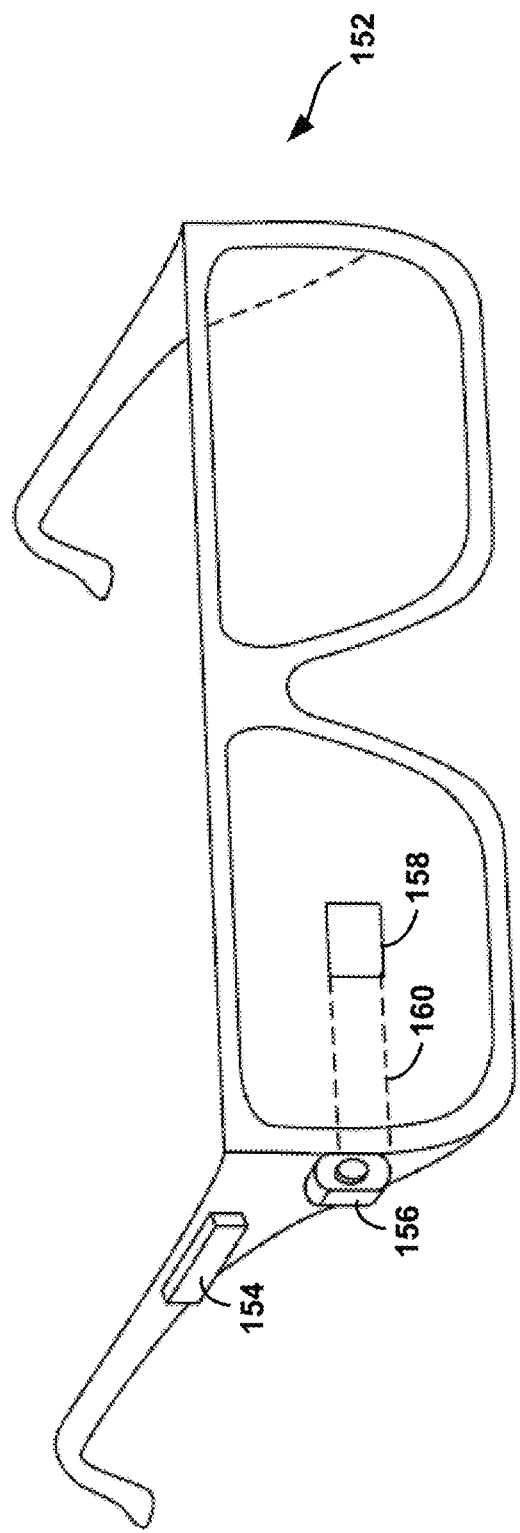
FIG. 1C illustrates another wearable computing system according to an example embodiment.

FIG. 1C illustrates another wearable computing system according to an example embodiment, which takes the form of an HMD 152. The HMD 152 may include frame elements and side-arms such as those described with respect to FIGS. 1A and 1B. The HMD 152 may additionally include an on-board computing system 154 and an image capture device 156, such as those described with respect to FIGS. 1A and 1B. The image capture device 156 is shown mounted on a frame of the HMD 152. However, the image capture device 156 may be mounted at other positions as well.

As shown in FIG. 1C, the HMD 152 may include a single display 158 which may be coupled to the device. The display 158 may be formed on one of the lens elements of the HMD 152, such as a lens element described with respect to FIGS. 1A and 1B, and may be configured to overlay computer-generated graphics in the user's view of the physical world. The display 158 is shown to be provided in a center of a lens of the HMD 152, however, the display 158 may be provided in other positions, such as for example towards either the upper or lower portions of the wearer's field of view. The display 158 is controllable via the computing system 154 that is coupled to the display 158 via an optical waveguide 160.

Figure 1D:
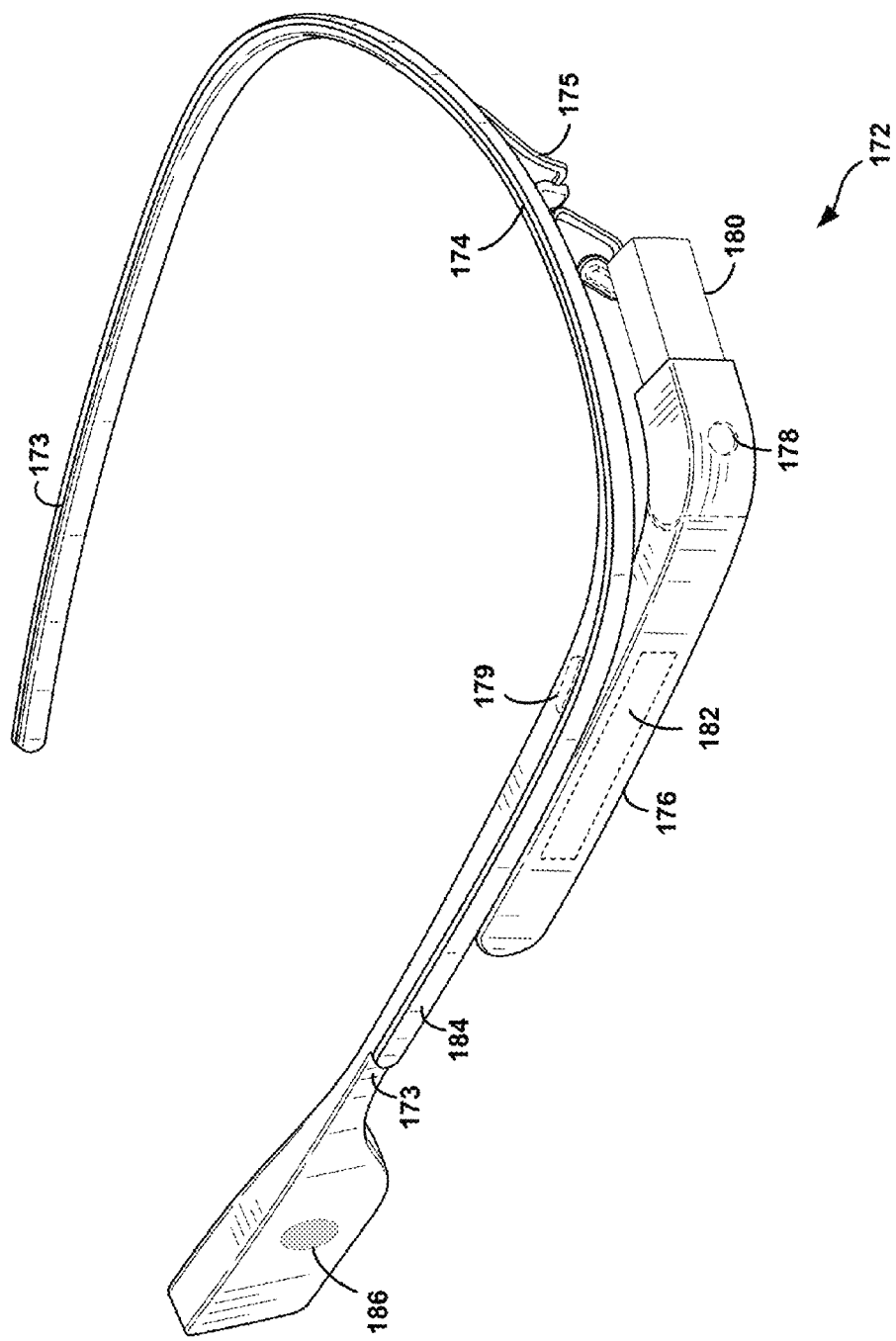
FIG. 1D illustrates another wearable computing system according to an example embodiment.

FIG. 1D illustrates another wearable computing system according to an example embodiment, which takes the form of a monocular HMD 172. The HMD 172 may include side-arms 173, a center frame support 174, and a bridge portion with nosepiece 175. In the example shown in FIG. 1D, the center frame support 174 connects the side-arms 173. The HMD 172 does not include lens-frames containing lens elements. The HMD 172 may additionally include a component housing 176, which may include an on-board computing system (not shown), an image capture device 178, and a button 179 for operating the image capture device 178 (and/or usable for other purposes). Component housing 176 may also include other electrical components and/or may be electrically connected to electrical components at other locations within or on the HMD. HMD 172 also includes a BCT 186.

The HMD 172 may include a single display 180, which may be coupled to one of the side-arms 173 via the component housing 176. In an example embodiment, the display 180 may be a see-through display, which is made of glass and/or another transparent or translucent material, such that the wearer can see their environment through the display 180. Further, the component housing 176 may include the light sources (not shown) for the display 180 and/or optical elements (not shown) to direct light from the light sources to the display 180. As such, display 180 may include optical features that direct light that is generated by such light sources towards the wearer's eye, when HMD 172 is being worn.

In a further aspect, HMD 172 may include a sliding feature 184, which may be used to adjust the length of the side-arms 173. Thus, sliding feature 184 may be used to adjust the fit of HMD 172. Further, an HMD may include other features that allow a wearer to adjust the fit of the HMD, without departing from the scope of the invention.

Further, although not explicitly shown in the FIGS. 1A to 1D, HMDs, such as HMDs 102, 152, and/or 172, could include an eye-tracking system or a portion of such a system. In an example embodiment, the HMD could include inward- or rearward-facing (i.e., eye-facing) light source(s) and/or camera(s) to facilitate eye-tracking functions. For example, an HMD may include inward-facing light sources, such as an LED(s), at generally known location(s) with respect to one another and/or with respect to an eye under observation. The inward-facing camera may therefore capture images that include the reflections of the light source(s) off the eye; or in other words, images that capture the controlled glints that correspond to the inward-facing light sources. As such, the positioning of the controlled glints in given image may be indicative of the position of the eye at the time the image was captured.

In a further aspect, with the above configuration, successive video frames may capture movement of the controlled in the image plane as the one or more eyes move. Thus, with the relative geometry of the controlled light source and the one or more eyes known, the observed movement of the controlled glints in the image plane may be analyzed in order to measure the movement of the eye.

Figure 1E:
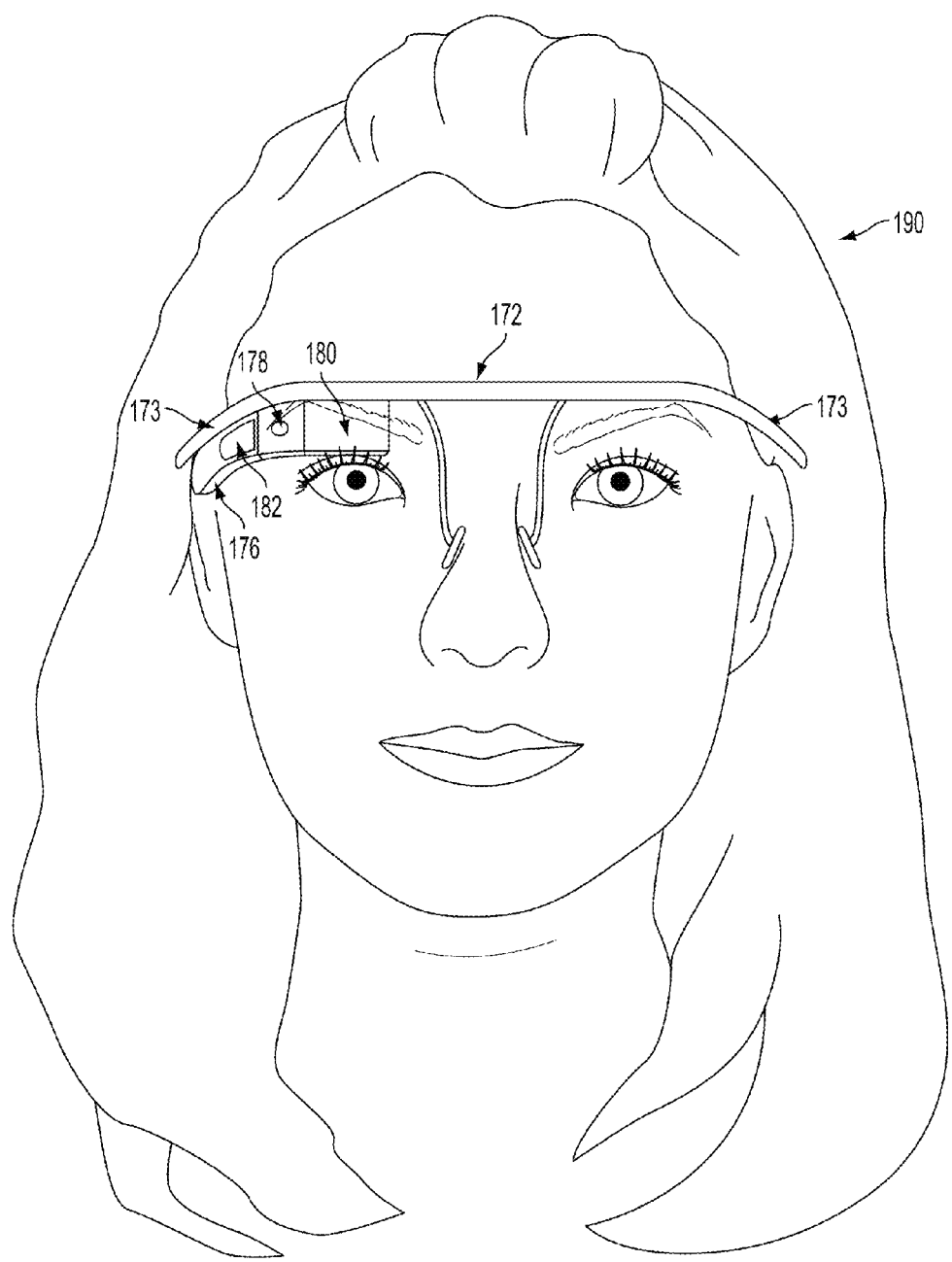
FIGS. 1E to 1G are simplified illustrations of the wearable computing system shown in FIG. 1D, being worn by a wearer.
Figure 1F:
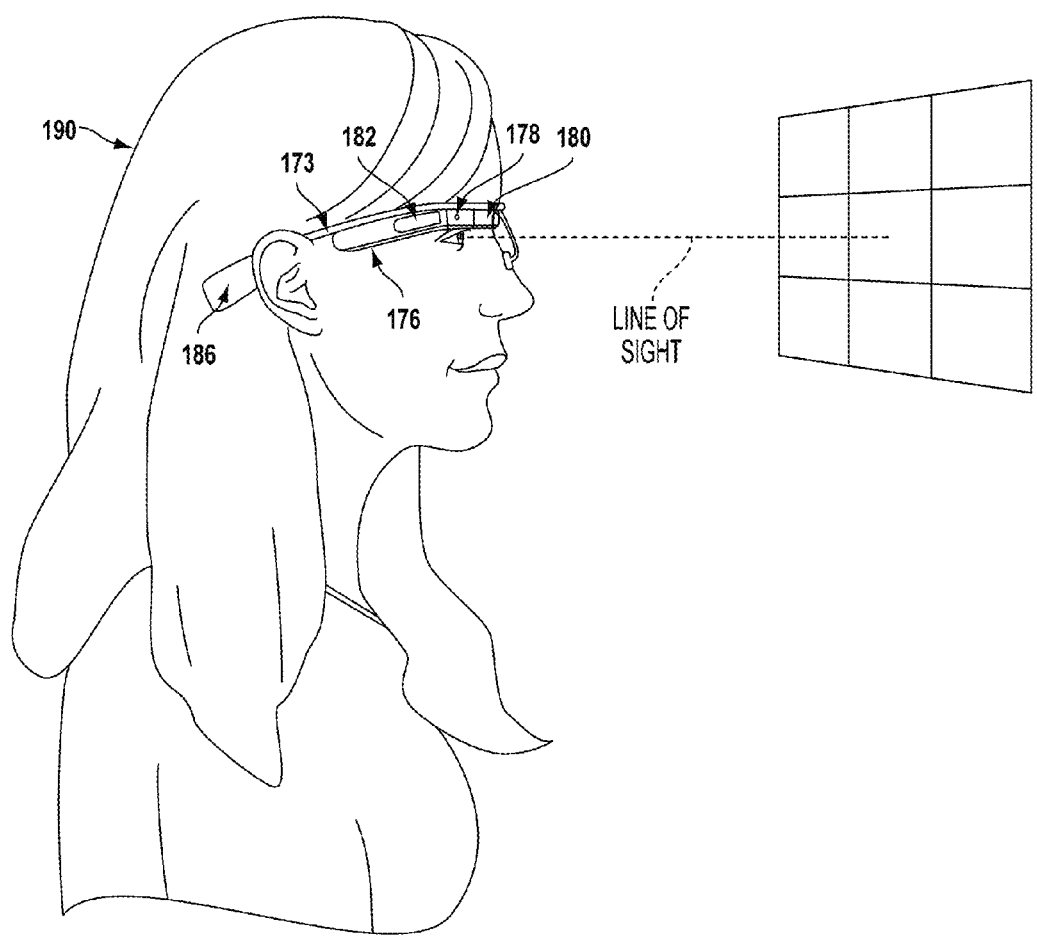
Figure 1G:
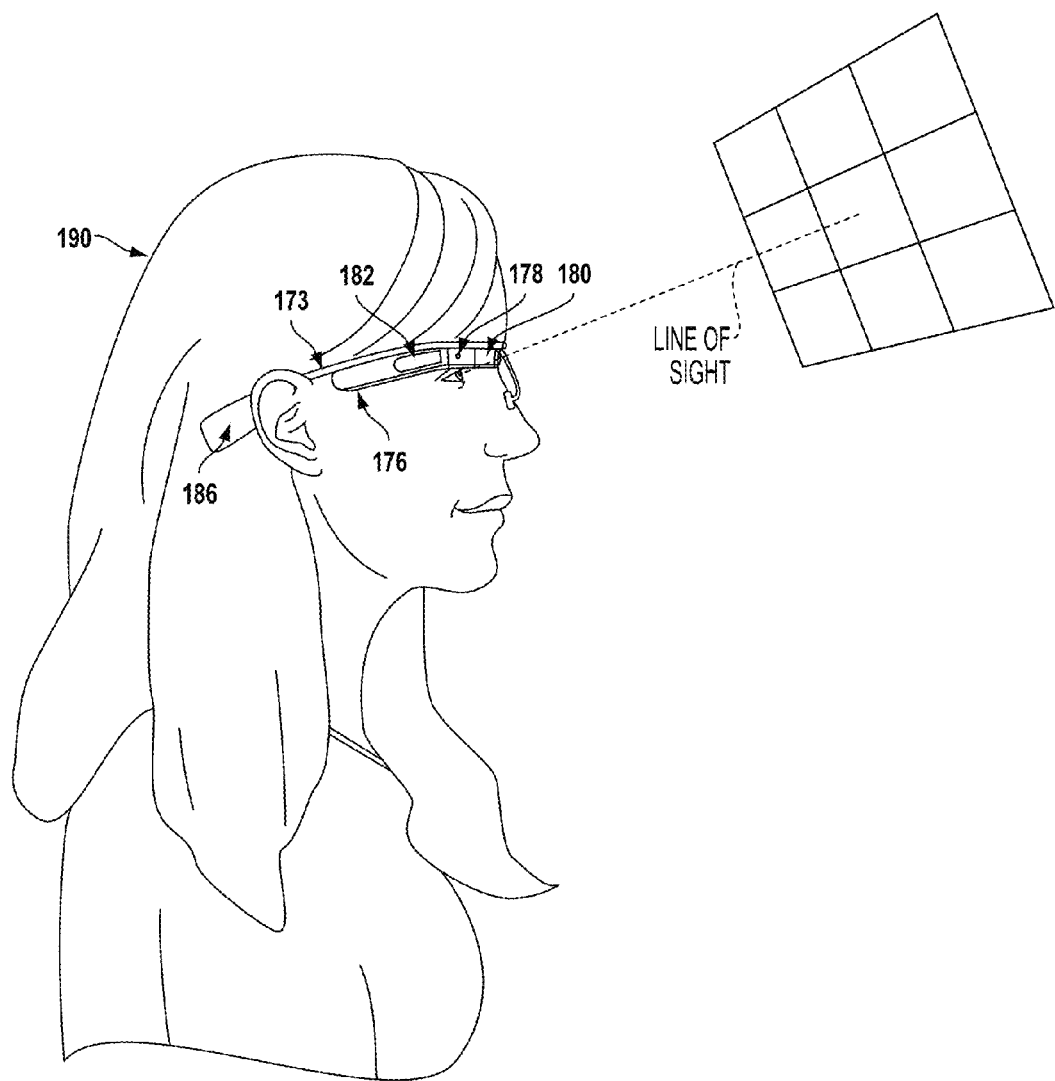

FIGS. 1E to 1G are simplified illustrations of the HMD 172 shown in FIG. 1D, being worn by a wearer 190. As shown in FIG. 1F, BCT 186 is arranged such that when HMD 172 is worn, BCT 186 is located behind the wearer's ear. As such, BCT 186 is not visible from the perspective shown in FIG. 1E.

In the illustrated example, the display 180 may be arranged such that when HMD 172 is worn, display 180 is positioned in front of or proximate to a user's eye when the HMD 172 is worn by a user. For example, display 180 may be positioned below the center frame support and above the center of the wearer's eye, as shown in FIG. 1E. Further, in the illustrated configuration, display 180 may be offset from the center of the wearer's eye (e.g., so that the center of display 180 is positioned to the right and above of the center of the wearer's eye, from the wearer's perspective).

Configured as shown in FIGS. 1E to 1G, display 180 may be located in the periphery of the field of view of the wearer 190, when HMD 172 is worn. Thus, as shown by FIG. 1F, when the wearer 190 looks forward, the wearer 190 may see the display 180 with their peripheral vision. As a result, display 180 may be outside the central portion of the wearer's field of view when their eye is facing forward, as it commonly is for many day-to-day activities. Such positioning can facilitate unobstructed eye-to-eye conversations with others, as well as generally providing unobstructed viewing and perception of the world within the central portion of the wearer's field of view. Further, when the display 180 is located as shown, the wearer 190 may view the display 180 by, e.g., looking up with their eyes only (possibly without moving their head). This is illustrated as shown in FIG. 1G, where the wearer has moved their eyes to look up and align their line of sight with display 180. A wearer might also use the display by tilting their head down and aligning their eye with the display 180.

Figure 2:
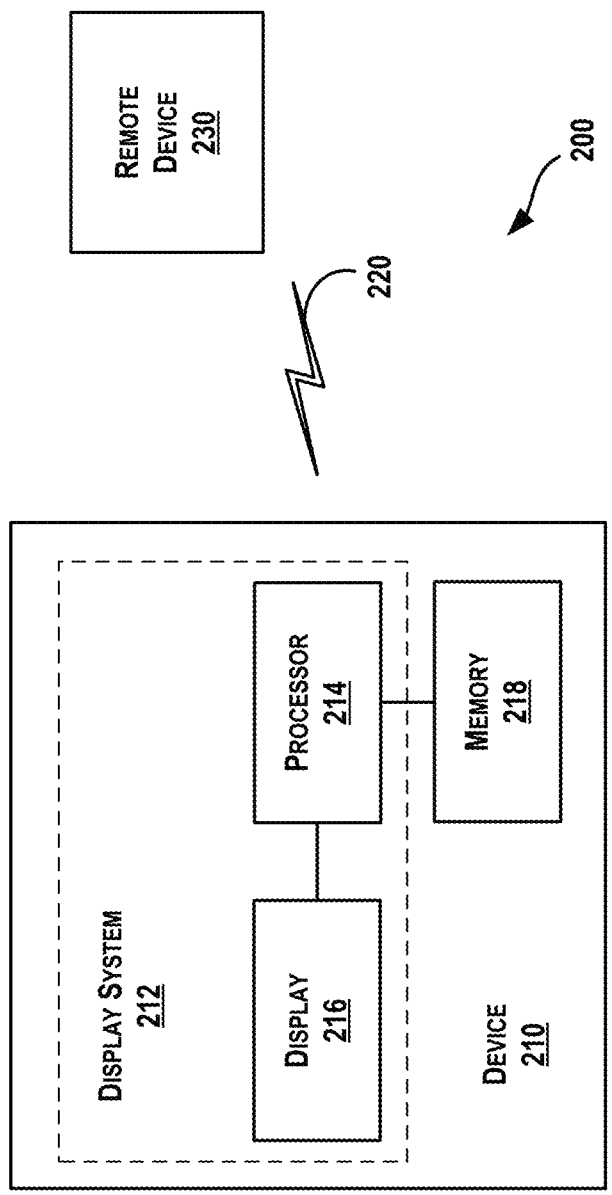
FIG. 2 is a simplified block diagram of a computing device according to an example embodiment.

FIG. 2 is a simplified block diagram a computing device 210 according to an example embodiment. In an example embodiment, device 210 communicates using a communication link 220 (e.g., a wired or wireless connection) to a remote device 230. The device 210 may be any type of device that can receive data and display information corresponding to or associated with the data. For example, the device 210 may take the form of or include a head-mountable display, such as the head-mounted devices 102, 152, or 172 that are described with reference to FIGS. 1A to 1G.

The device 210 may include a processor 214 and a display 216. The display 216 may be, for example, an optical see-through display, an optical see-around display, or a video see-through display. The processor 214 may receive data from the remote device 230, and configure the data for display on the display 216. The processor 214 may be any type of processor, such as a micro-processor or a digital signal processor, for example.

The device 210 may further include on-board data storage, such as memory 218 coupled to the processor 214. The memory 218 may store software that can be accessed and executed by the processor 214, for example.

The remote device 230 may be any type of computing device or transmitter including a laptop computer, a mobile telephone, head-mountable display, tablet computing device, etc., that is configured to transmit data to the device 210. The remote device 230 and the device 210 may contain hardware to enable the communication link 220, such as processors, transmitters, receivers, antennas, etc.

Further, remote device 230 may take the form of or be implemented in a computing system that is in communication with and configured to perform functions on behalf of client device, such as computing device 210. Such a remote device 230 may receive data from another computing device 210 (e.g., an HMD 102, 152, or 172 or a mobile phone), perform certain processing functions on behalf of the device 210, and then send the resulting data back to device 210. This functionality may be referred to as "cloud" computing.

In FIG. 2, the communication link 220 is illustrated as a wireless connection; however, wired connections may also be used. For example, the communication link 220 may be a wired serial bus such as a universal serial bus or a parallel bus. A wired connection may be a proprietary connection as well. The communication link 220 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. The remote device 230 may be accessible via the Internet and may include a computing cluster associated with a particular web service (e.g., social-networking, photo sharing, address book, etc.).

In some embodiments, an HMD may be a modular, such that various components of a modular HMD system can be swapped in and out for one another. A modular HMD system includes components that can be attached together to form a fully functioning HMD. For example, an HMD may be formed from a modular HMD system by selecting at least one component from each of certain component categories, and attaching the selected components to one another to form the HMD. Further, a modular HMD system may provide modularity by including multiple components in at least one core component category, which are each interchangeable with other components in the same category (e.g., such that the user can readily change the way their HMD looks and/or functions by swapping one component for another in the same category). Further, a modular HMD system may include optional components, which can be integrated into a modular HMD, but are not required to form a fully functioning HMD. Examples of such component categories could include, but are not limited to, frames (with or without lenses), lenses, displays, cameras, chipsets, processors, memory, aesthetic attachments, input devices, and combinations of the foregoing, among other possibilities.

Figure 3:
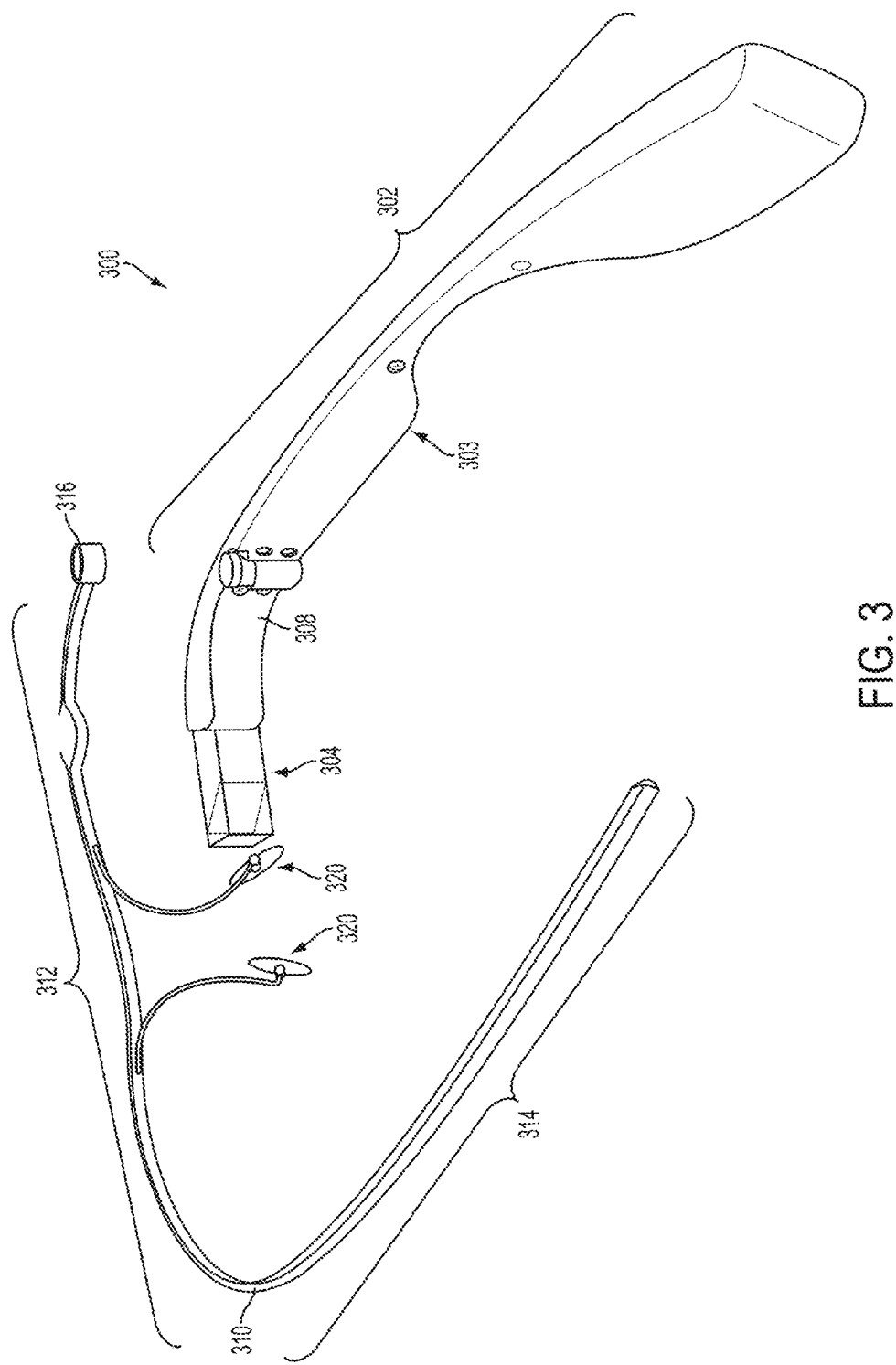
FIG. 3 is an illustration of a modular HMD system, according to an example embodiment.

FIG. 3 is an illustration of a modular HMD system 300, according to an example embodiment. The modular HMD system 300 includes a core component 302, which may provide the core electrical components, and perhaps all of the electrical components, for the modular HMD. For instance, core component 302 provides one side-arm 303 of the HMD, a see-through display 304, a camera, various sensors, a battery, an on-board computing system, wired and/or wireless communication interface(s), and/or communication port(s), among other possibilities.

In some embodiments, a modular HMD system may include two or more different and interchangeable core components. For example, a modular HMD system could include core component 302 and one or more other core components which could be exchanged with core component 302 by a user. Each of the other core components could differ from core component 302 by, e.g.: (a) including a different type of side-arm, (b) including a different type of display, (c) including a different camera and/or a different number of cameras (and possibly no cameras), (d) including different sensors, more or less of the same sensors, and/or a different arrangement of sensors on the core component, (e) including a different battery, (f) including a different on-board computing system, (g) including different wired and/or wireless communication interface(s), and/or (h) including different communication port(s), among other possibilities.

The modular HMD system 300 also includes a frame component 310 with a front side 312 and a side arm 314. Further, frame component 310 includes a male attachment feature 316 that corresponds to a female attachment feature 308 on the core component 302, such that the frame component 310 may be attached to the core component 302. Thus, when attachment feature 316 is inserted into attachment feature 308, the core component 302, such that the frame component 310 may collectively form an HMD with a complete support structure (e.g., two side-arms and a front section with nose pads 320). Further, frame component 310 may be interchangeable with other types of frame components, which may include different types of lenses (e.g., sunglass lenses or prescription lenses).

III. EXAMPLE SYSTEMS WITH CODED LENS

As noted above, in a modular HMD system, where different types of lenses are available and swappable by a user, it may be desirable to provide a mechanism by which other components of the system can quickly and discretely ascertain which lens is currently attached to the HMD (e.g., with little, and perhaps no, intervention by the user). Provided with such information other components of the modular system (e.g., core component 302) may be configured to detect when a new lens is attached to the HMD, and responsively update processes that can vary according to the particular lens that is attached. As further noted above, such processes may rely upon reflections off of an inner surface of a lens for determining eye position and/or movement. One example of such a process will be described in greater detail in Section IV below.

Figure 4A:
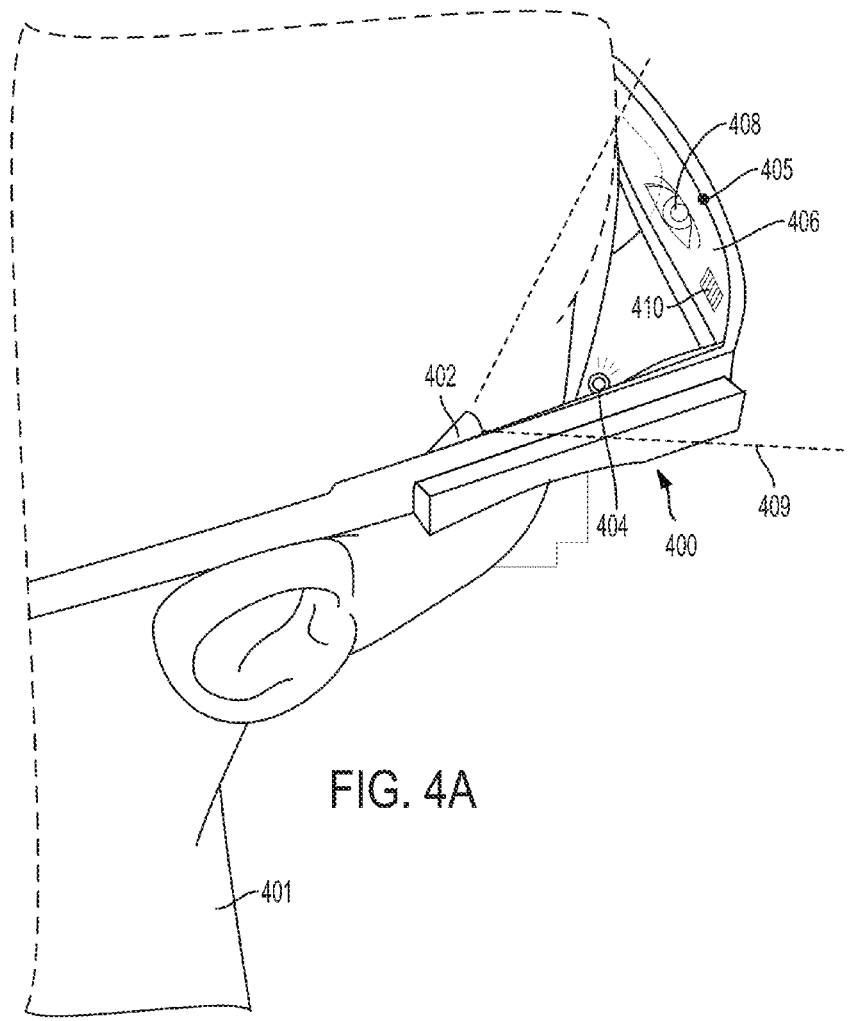
FIG. 4A is an illustration showing an HMD having a coded lens, according to an example embodiment.

FIG. 4A is an illustration showing an HMD 400 having a coded lens 406, according to an example embodiment. In FIG. 4A, HMD 400 is shown as being worn by a wearer 401. Note that while HMD 400 is described separately below, it should be understood that HMD 400 may be the same as or similar to any of the HMDs described in reference to FIGS. 1A to 3. Further, components of HMD 400 may function in the same or a similar manner as corresponding types of components of the HMDs described in reference to FIGS. 1A to 3. Of course, it should be understood that HMD 400 and/or its components may differ from the HMDs and HMD components described in reference to FIGS. 1A to 3.

Referring to FIG. 4A in greater detail, HMD 400 includes: (a) an IR camera 402 having a field of view that includes the lens 406, (b) a first IR light source 404 for illuminating the lens 406, (c) a second IR light source 405 that is facing inward and arranged to illuminate the wearer's eye with infrared "glints" (e.g., dots, which can be reflected off the eye, and then off of the inner surface of the lens 406, such that they can be detected by the IR camera 402). This system may provide eye tracking by illuminating the eye with glints from the second IR light source 405, and analyzing the shape and position of the glints in IR image data of the lens 406 that is captured by IR camera 402.

Further, lens 406 includes an IR-detectable machine-readable code 410, which is formed by a variable IR-interaction pattern in the coating on the inner surface of the lens 406. Accordingly, when the lens 406 is illuminated by the IR light source 404, the machine-readable code 410 may be visible in image data captured by the IR camera 402. As such, an onboard computer in the HMD may detect the machine-readable code 410 in image data captured by IR camera 402, and responsively perform a process to re-calibrate an eye-analysis process (such as an eye-tracking process) based on the characteristics of the lens indicated by the machine-readable code 410. Further, note that lens 406 may be configured to serve as a graphic display, but could also be a lens that is otherwise similar to traditional eyeglasses or sunglasses.

In an example embodiment, an HMD's onboard computing system may include program instructions, stored in a non-transitory computer readable medium, which are executable to: (a) receive infrared (IR) image data of an inner surface of a lens of an HMD, where the image data is captured while the inner surface of the lens is illuminated with infrared light, (b) detect, in the IR image data, a reflection of an eye area that is reflected from the inner surface of the lens; (c) detect, in the IR image data, a machine-readable code resulting from a variable IR interaction pattern on a surface of the lens; (d) calibrate an eye-analysis process based on the determined lens type; and (e) apply the eye-analysis process to the reflection of the eye to determine position data corresponding to the eye. Alternatively, some or all of such program logic may be executed at a remote computing device on behalf of the HMD (e.g., in a "cloud" computing arrangement).

Various arrangements of IR camera 402 and IR light source 404 on an HMD are possible. For example, in order to capture an image that includes the inner surface of the HMD lens 106, IR camera 402 is arranged on an inner surface of the side arm of HMD 100. Configured as such, when the HMD 400 is worn, the lens of the camera 402 is generally directed towards and has a field of view 409 that substantially includes the HMD lens 106. Similarly, IR light source 104 is arranged on an inner surface of the side arm of HMD 400, such that when the HMD 400 is worn, IR light emitted from the light source 404 illuminates at least the portion of the lens 406 that includes the machine-readable code 410.

Note that the field of view 402 of camera 402 may be considered to substantially include the HMD lens 406, so long as the field of view includes a portion of lens 106 from which the machine-readable code 410 can be ascertained. Further, in embodiments where image data from camera 402 is also used to detect controlled glints (e.g., for purposes of an eye-tracking process), the field of view 402 may be considered to substantially include the HMD lens 406 if it includes a portion of lens 406 from which both the machine-readable code 410 and the controlled glints can be ascertained.

Various types of IR cameras may be utilized. Generally, an IR camera 402 may be any camera that is operable to detect wavelengths in the infrared spectrum, e.g., by sensing or detecting black-body radiation. Further, an IR camera 402 may be operable to create image data that represents IR wavelengths in the visible spectrum, such as a thermogram. Note that an IR camera may also be referred to as a thermographic camera or a thermal imaging camera. In an HMD, it may be desirable to use an uncooled IR camera, although any type of IR camera could theoretically be utilized.

Note various arrangements of an IR light source 404 and/or IR camera 402 may be utilized to illuminate and capture image data of a variable IR interaction pattern formed by a selectively applied optical coating on a lens. In general, the IR camera and IR light source may be placed in any arrangement on an HMD, so long as when the HMD is worn, the IR light source illuminates the machine-readable code, and the IR camera includes the machine-readable code (and possibly the reflection of the eye and controlled glints) in its field of view. Additionally, in some embodiments, more than one IR camera may be used to capture IR image data of a lens, and/or more than one IR light source may be used to illuminate a variable IR interaction pattern forming a machine-readable code 410 on a lens. In other embodiments, it also possible that a single IR light source or cluster of light sources may be arranged on an HMD such that the single source can illuminate the machine-readable code 410 and emit the focused points or beams of light towards the eye that provide controlled glints.

Figure 4B:
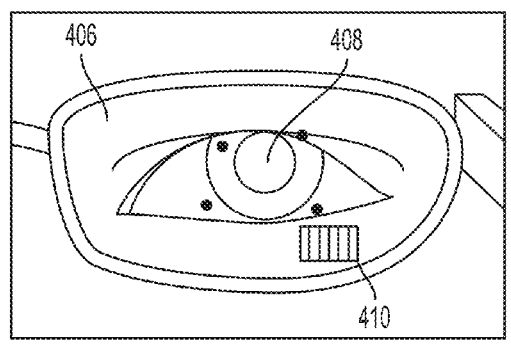
FIG. 4B is an illustration of an IR image that was captured by an IR camera, according to an example embodiment.

FIG. 4B is an illustration of an IR image that was captured by an IR camera 402, according to an example embodiment. As shown, the image may include a number of glints in the eye area 408 (or more precisely, in the reflection of the eye area on the lens), which result from a glint pattern that is emitted by the second IR light source 405, then reflects off of the wearer's eye area and onto the inner surface of lens 406, such that IR camera 402 can capture the reflection of the glints in image data of the lens 406. (Note that in FIG. 4B, the glints are shown as black dots over the eye area 408, but are not explicitly labeled.) Further, the image shown in FIG. 4B includes a machine-readable code 410. In the example shown in FIG. 4B, machine-readable code 410 is a bar code. (Of course, other types of codes or information can also be provided by way of a variable IR interaction pattern on a lens.)

Lens 406 may be selectively coated to form the machine-readable code 410. For example, the dark portions of bar code 410 may result from areas of lens 406 that are coated with an IR reflective material, while the light portions of bar code 410 may result from areas of lens 406 that are not coated with an IR reflective material. Further, the lens 406 may be constructed of a material with a high IR transmittance or absorptivity, which may result in the contrast between the light and dark portions of the machine-readable code 410 being more pronounced. Note that the pattern that makes up a machine-readable code may be formed by the dark portions in the IR image (meaning that the portions of the lens having the reflective coating define the shape of the code), or may be formed by the light portions in the IR image (meaning that the portions of the lens without the reflective coating define the shape of the code).

A variable IR interaction pattern forming the machine-readable code 410 may be provided by applying various types of optical coating to a lens. The particular optical coating, or the particular combination of optical coatings, may vary in different embodiments. For example, various metal coatings and/or various dielectric coatings may be applied to a lens 406 to form a variable IR interaction pattern on the lens that reflects IR wavelengths in the shape of machine-readable code 410 (or in a shape that outlines machine-readable code 410). Further, the optical coating or combination of optical coatings that is applied to form a variable IR interaction pattern on a lens may be partially or completely transparent, such that the pattern does not distract the wearer of an HMD with such a lens.

Note that a lens may include various types of machine-readable codes and/or other machine-readable information, which may or may not be human-readable. For instance, the machine-readable code could be a standard QR code or bar code format. However, other code formats may be utilized. Further, in some implementations the code might provide some assistance in ascertaining the characteristics. For example, IR reflective coating could form an outline of the lens, which may provide an indication of the size and shape of the lens. As another example, IR reflective material may form perpendicular straight lines on the surface of the lens, which may provide an indication of the orientation of the lens and of its base curvature (e.g., when an image of the straight line is captured by a camera with a rectilinear lens).

Figure 5A:
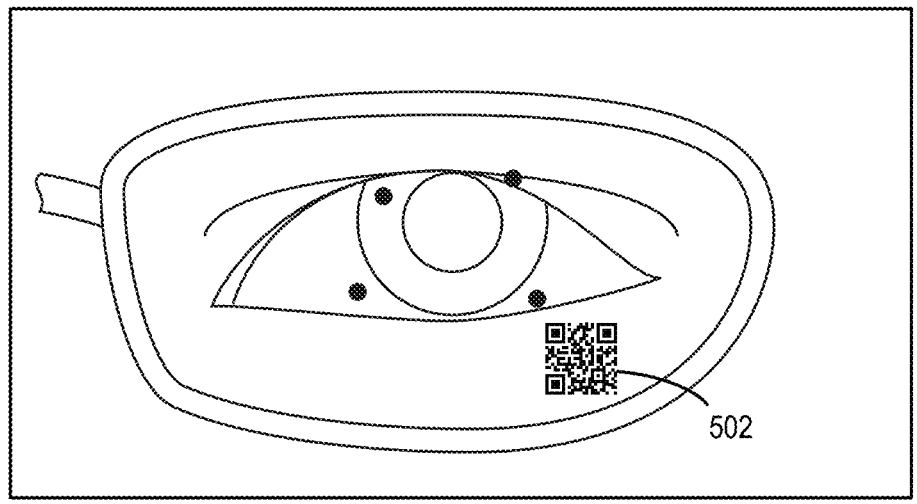
FIG. 5A is an illustration of an IR image that was captured by an IR camera, and includes another variable IR interaction pattern on a lens, according to an example embodiment.

FIG. 5A is an illustration of an IR image 500 that was captured by an IR camera 402, according to an example embodiment. FIG. 5A includes another variable IR interaction pattern on a lens, according to an example embodiment. As shown, the image 500 may include a number of controlled glints 510 in a reflection of an eye area onto the lens. The controlled glints 510 form a glint pattern, which may facilitate an eye-tracking process according to an example embodiment. Further, in FIG. 5A, an optical coating is selectively applied to form a variable IR interaction pattern in the shape of a QR code 502. Note that the dark portions of QR code 502 may be formed by areas that are coated with an optical coating that is highly reflective of IR wavelengths, while the light portions of QR code 502 may be formed by areas that lack any coating or have a different coating (e.g., that is detectably less reflective of IR wavelengths and/or that is IR absorptive).

Figure 5B:
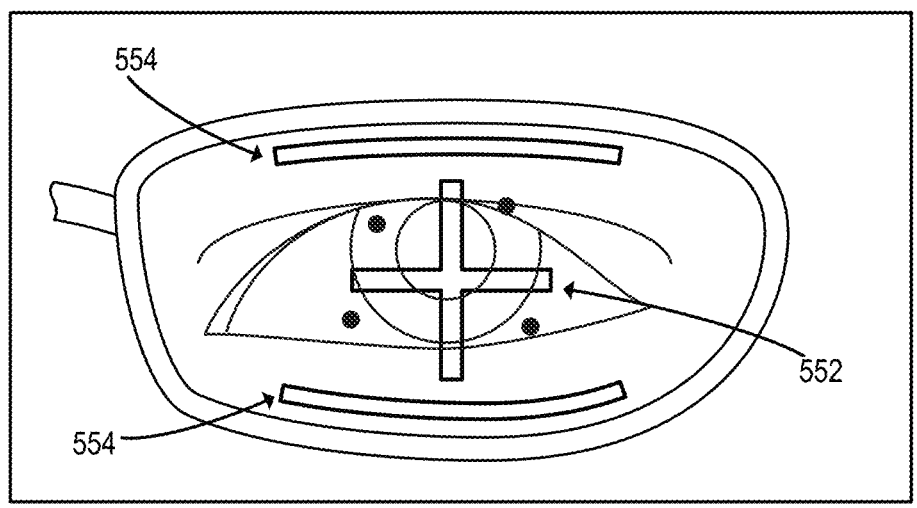
FIG. 5B is an illustration of another IR image that was captured by an IR camera, which includes yet another variable IR interaction pattern on a lens, according to an example embodiment.

FIG. 5B is an illustration of another IR image 550 that was captured by an IR camera 402, which includes yet another variable IR interaction pattern on a lens, according to an example embodiment. As shown, the image 550 may include a number of controlled glints 560 in a reflection of an eye area onto the lens. The controlled glints 560 form a glint pattern, which may facilitate an eye-tracking process according to an example embodiment. Further, in FIG. 5A, an optical coating is selectively applied to form a variable IR interaction pattern that includes a cross 552 and lines 554. This relatively simple pattern (as compared to, e.g., a QR code) could still be used to identify a particular type lens. In this type of simple coding system, different types of lenses could be identified by, e.g., varying the number of lines and/or the orientation of various lines with respect to the cross 552.

Further, cross 552 and/or lines 554 may provide information that make it easier to identify the lens and/or determine the one or more characteristics of the lens. As such, cross 552 and/or lines 554 may improve the ability of an HMD to identify a new lens and/or to automatically adjust an eye-tracking process and/or other lens-dependent processes, when a user changes the lens (or lenses) on their modular HMD. For example, lines 554 could follow the shape of the frame, and thus may provide an indication of the shape and/or size of the lens, which can in turn be used to help identify the particular lens, or at least the type of lens. Additionally or alternatively, cross 552 may be formed by perpendicular lines on the surface of the lens, which are applied along two axes of the lens. Further, in some embodiments, the perpendicular lines forming cross 552 may intersect at a center point of the lens. As such, cross 552 may be used to help to identify an orientation on the wearer (e.g., with respect to the wearer's eye area) and/or to help determine the shape of the lens.

Further, if the lines forming cross 552 are applied along the planes of two axes of the lens, the lines will follow the curvature of the lens in these planes. Additionally, the lens of the IR camera (e.g., a rectilinear lens) may have known optical characteristics, which may cause the lines forming cross 552 to appear curved in two-dimensional image data. As such, the amount of apparent curvature in an IR image of cross 552 may be used to help determine the base curvature of the particular lens.

In some implementations, an RFID tag may be embedded in an eyeglass lens or frame. The RFID tag can identify the particular lens (or at least the type or model of lens). As such, an example method may use the RFID tag to identify a particular lens (and thus its characteristics), instead of using a machine-readable code formed by a variable IR interaction pattern on the lens. As yet another alternative, an example method could identify a lens by way of a specific combination of an RFID tag and a variable IR interaction pattern (and possibly other identifying information as well). In yet other implementations, computer vision techniques may be utilized to identify a particular lens, instead of or in combination with a variable IR interaction pattern forming a machine-readable code.

IV. EXAMPLE METHODS

Figure 6:
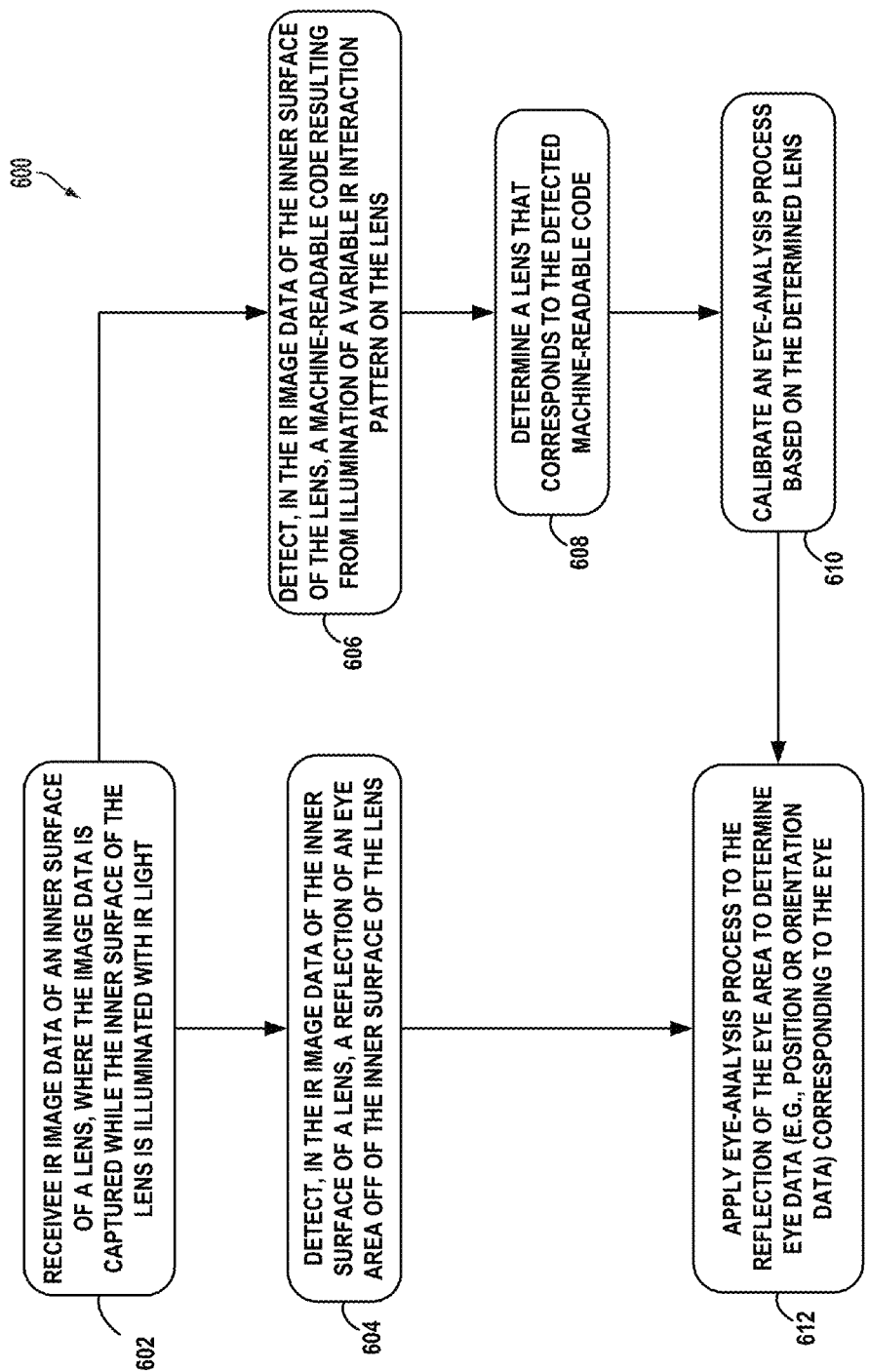
FIG. 6 is a flow chart illustrating a method, according to an exemplary embodiment.

FIG. 6 is a flow chart illustrating a method 600, according to an example embodiment. Exemplary methods, such as method 600, may be carried out in whole or in part by a wearable computing system having a head-mountable display (e.g., by components and/or systems of a head-mountable device). For explanatory purposes, the description below may simply refer to method 600 as being carried out by a computing system. However, it should be understood that method 600 or portions thereof may be carried out various types of devices including but not limited to an HMD, and may also be carried out by various combinations of an HMD and/or other computing devices, without departing from the scope of the invention.

Further, it should be understood that an example method such as method 600 may also be carried out in whole or in part by a device or system, or by a combination of one or more devices and/or one or more systems, that are in communication with and can receive data from a device or system that captures the IR image data (e.g., from an HMD). For example, an exemplary method may be implemented in whole or in part by a server system (e.g., a cloud server), which receives data from a computing system such as an HMD.

As shown by block 602, method 600 involves a computing system receiving IR image data of an inner surface of a lens of an HMD, where the image data is captured while the inner surface of the lens is illuminated with IR light (i.e., electromagnetic waves in the infrared spectrum). Accordingly, in some embodiments, an example method may further involve the computing system operating an IR light source that is arranged to illuminate the inner surface of the HMD lens and, while the inner surface of the HMD lens is illuminated, operating an IR camera to capture the IR image data of the lens.

At block 604, the computing system detects, in the IR image data of the inner surface of a lens, a reflection of an eye area on the inner surface of the lens. Further, the computing system detects, in the IR image data of the inner surface of the lens, a machine-readable code resulting from illumination of a variable IR interaction pattern on the lens, as shown by block 606. The computing system then determines a lens that corresponds to the detected machine-readable code, as shown by block 608. The computing system can then calibrate an eye-analysis process based on the determined lens, as shown by block 610. In an example embodiment, the eye-analysis process may be an eye-tracking or eye-positioning process, or any other process that detects or determines eye gestures, eye movements, position, and/or orientation of an eye. Then, after calibrating the eye-analysis process, the eye-analysis process may be applied to the reflection of the eye area to determine eye data (e.g., position or orientation data) corresponding to the eye, as shown by block 612.

As noted above, block 608 involves the computing system determining a lens that corresponds to the machine-readable code that was detected on the lens. In some cases, each lens that is manufacture may be identified by its own unique machine-readable code. In other cases, a unique machine-readable code may identify each of a plurality of types of lenses (e.g., so that all lenses of the same type will have the same machine-readable code). Further, in some embodiments, the machine-readable code on the lens may identify a component that includes the lens and at least a portion of the HMD frame (e.g., frame component 310 shown in FIG. 3). Machine-readable codes on lenses may also be used to identify other types of components and structures that include a lens.

As noted above, block 610 involves the computing system calibrate the eye-analysis process based on the determined lens. In an example embodiment, this function may involve making one or more adjustments to the eye-analysis process based on one or more characteristics of the determined lens type. In particular, the eye-analysis process may be adjusted to account for one or more characteristics of the particular lens (or the particular type of lens), such as one or more of: (a) pantoscopic tilt of the lens, (b) wrap of the lens, and (c) curvature of the lens (e.g., base curvature), among other possibilities.

As a specific example, when controlled glints are detected in the IR image data of the eye area, the spacing of the glints from the same glint pattern can differ between reflections from different types of lenses (e.g., due to different curvatures of the different lenses). Accordingly, the characteristics of the determined lens may be used to calibrate an eye-tracking process based on controlled glints, by adjusting the determined positions and/or spacing of glints to account for the curvature and/or other characteristics of the particular lens that is attached to a modular HMD at a given point in time.

Further, in an embodiment where the machine-readable code on the lens identifies a frame component that includes the lens, one or more characteristics of the frame, such as the distance the frame holds the lens from the eye and/or the angle at which the frame holds the lens with respect to the eye, may also be used to calibrate an eye-analysis process. For example, when controlled glints are detected in the IR image data of the eye area, the spacing of the glints from the same glint pattern can vary according to how a frame component positions and orients the lens with respect to the eye. Accordingly, one or more characteristics of the frame component may be used in the calibration of an eye-tracking process based on controlled glints; e.g., adjusting the determined position(s) and/or spacing of glints to account for the location and/or orientation at which the frame holds the detected lens with respect to the wearer's eye area.

In a further aspect, an example method such as method 600 may be automatically initiated whenever the computing system detects a new lens has been attached to a modular HMD. For example, referring back to FIG. 3, when the male attachment feature 316 of frame component 310 is attached to the female attachment feature 308 on the core component 302, electrical leads on male attachment feature 316 may complete a circuit to indicate a frame component (and thus any lens that is part of the frame component) is attached. Accordingly, then the HMD detects a frame-component detachment event followed by a frame-component attachment event, it may be interpreted to mean that a new lens is attached to the HMD. As such, the HMD may responsively implement method 600 (or at least portions thereof) to calibrate an eye-analysis process. In particular, the HMD may detect, in subsequent IR image data of the inner surface of the lens, a second machine-readable code resulting from a different IR interaction pattern, and responsively: (i) determine a second lens type that corresponds to the second machine-readable code, and (ii) recalibrate the eye-analysis process based on the second lens type.

V. ILLUSTRATIVE EYE-TRACKING BASED ON CONTROLLED GLINTS

Some eye-tracking techniques utilize "controlled glints" to determine eye movements. A system that facilitates eye-tracking based on controlled glints may include a number of light sources that are directed at an eye area, such that the reflections of these light sources from the eye (i.e., the controlled glints) may be recorded by a video camera that is also directed at the eye (or directed at another surface that redirects the reflections from the eye, such as the lens 402 shown in FIGS. 4A and 4B). The controlled glints may then be analyzed to determine the general position of the eye.

As a specific example, four light sources may be configured to provide a square or rectangular arrangement of glints on the eye. However, due to the shape of the eye, the generally square arrangement of glints will be warped according to the position of the eye. Accordingly, the manner in which the arrangement of glints warps from frame to frame may be analyzed to determine how the eye has moved between frames.

More specifically, to determine eye movement from controlled glints, frames of the video image may be flattened. The flattening process maps the ellipsoid shape of the corneal surface of the eye to a two-dimensional image, such that the actual distance between glints on the corneal surface is represented in the two-dimensional image. An exemplary system may then determine optical flow between the flattened frames, which is indicative of how the glints moved between frames. The optical flow may then be re-mapped to the corneal surface in order to determine how the eye has moved.

While the above example may be an efficient technique for eye-tracking in some scenarios, ambient light can often interfere with controlled glints. More specifically, ambient light may also reflect of the eye and create "ambient glints," which may also be captured by the video of the eye. In some instances, the ambient-light reflections may make it difficult or even impossible to determine whether a glint is a controlled glint or an ambient glint. Thus, ambient light can make eye-tracking data based on controlled glints inaccurate.

In order to help distinguish controlled glints from ambient glints, an exemplary embodiment may switch off one light source in each frame, and rotate the light source that is switched off. For example, consider the above example with four light sources configured to provide a generally square arrangement of controlled glints. In this configuration, an exemplary system may switch off one light source during each frame of the video, rotating the switched-off light source such that each light source is switched off every fourth frame. As such, the general structure of the controlled glints will be known in each frame, which may help to distinguish the controlled glints from ambient glints.

In a further aspect of an exemplary embodiment, the light sources and the video camera to capture the glints may be implemented on a wearable computer with a head-mounted display (HMD). In particular, the lens frame of a glasses-style HMD may include an array of inward-facing light sources (e.g., LEDs) and an inward-facing video camera, which are both directed at the eye.

A. Exemplary HMD-Implemented Methods

Figure 7:
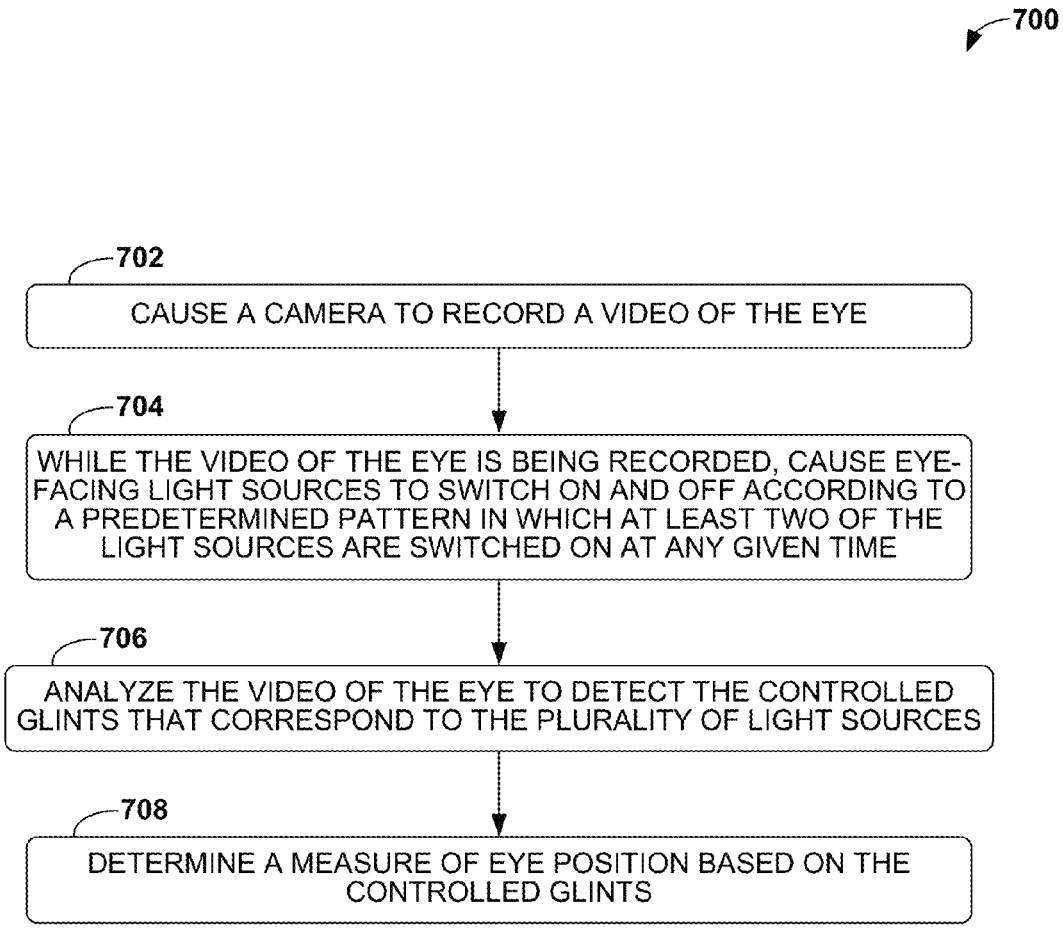
FIG. 7 is a flow chart illustrating a method for eye tracking using controlled glints, according to an exemplary embodiment.

FIG. 7 is a flow chart illustrating a method 700 for eye tracking using controlled glints, according to an exemplary embodiment. Exemplary methods, such as method 700, may be carried out in whole or in part by a wearable computer having a head-mountable display (which may further have an inward-facing camera, depending upon the particular implementation).

As shown by block 702 of FIG. 7, exemplary method 700 involves an HMD causing a camera that is attached to the HMD to record a video of the eye (or in other words, to capture a sequence of images of the eye). While the video of the eye is being recorded, the HMD causes a number (e.g., three or more) of eye-facing light sources, which may be attached to the HMD, to switch on and off according to a predetermined pattern in which at least two of the light sources are switched on at any given time while the video of the eye is being recorded, as shown by block 704. The HMD may then analyze the video of the eye to detect the controlled glints that correspond to the plurality of light sources, as shown by block 706. Then, the HMD may determine a measure of eye position based on the controlled glints, as shown by block 708.

i. Switching Light Sources on and Off According to a Predetermined Pattern

As noted above, at block 704, the light sources are switched on and off according to a predetermined pattern in which at least two light sources are switched on at any given point in time. As a general example, such a predetermined pattern may involve switching off just one of the light sources at a given time and changing the switched-off light source one or more times while the video of the eye is being recorded, according to a predefined schedule. Other general examples are also possible.

In some embodiments, the predetermined pattern may be a predetermined sequence of light-source combinations, with each combination having certain light sources that are turned on. Further, in such an embodiment, the sequence of light-source combinations may be repeated.

Figure 8A:
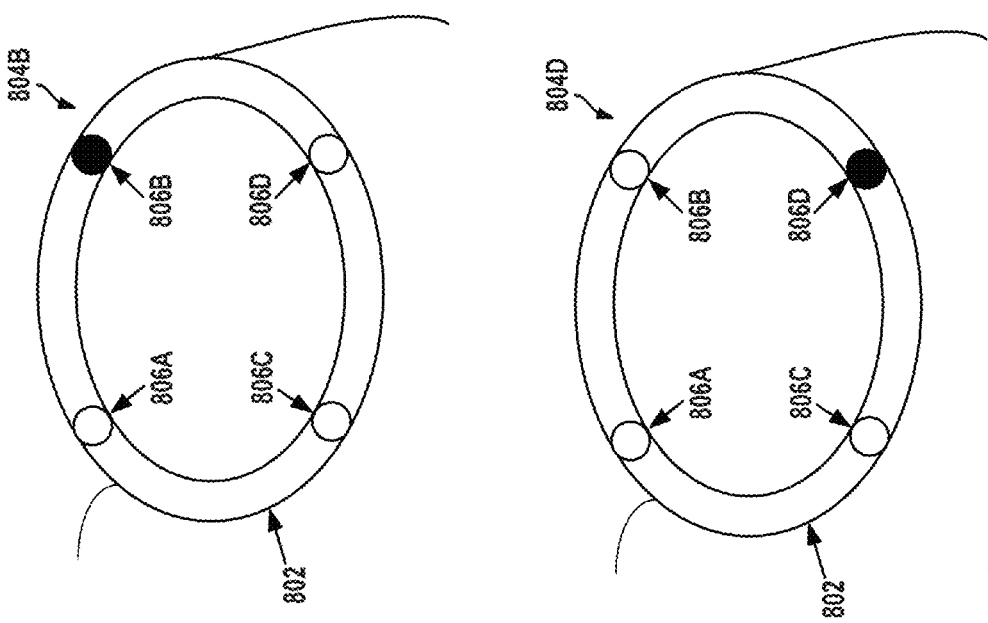
FIG. 8A is a simplified illustration of a predetermined sequence of light-source combinations, according to an exemplary embodiment.
Figure 8A:
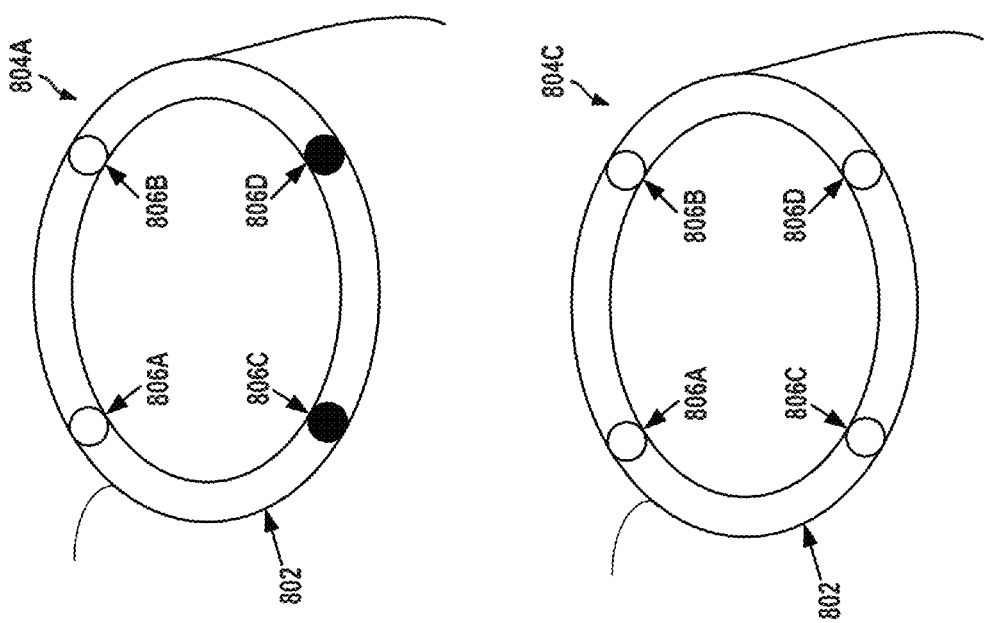

FIG. 8A is a simplified illustration of a predetermined sequence of light-source combinations, according to an exemplary embodiment. Specifically, FIG. 8A shows an HMD 802 going through a sequence of four light-source combinations 804A to 804D. To do so, HMD 802 includes four light sources 806A to 806D, which are attached to the frame of HMD 802 and have a substantially rectangular spatial relationship with one another. Configured as such, HMD 802 may individually switch light sources 806A to 806D on and off according to a predetermined pattern. (Note that for purposes of illustration in FIG. 8A, switched-off light sources are black and switched-on light sources are white.)

In the illustrated embodiment, the predetermined pattern may be the sequence of light-source combinations 804A to 804D. As such, the HMD 802 may initially turn on light sources 806A and 806B in order to form light-source combination 804A. Then, after a predetermined period of time, the HMD may turn on light sources 806A, 806C, and 806D to form light-source combination 804B. After again waiting the predetermined period of time, the HMD 802 may turn on all the light sources 806A to 806D to form light-source combination 804C. Next, and again after waiting the predetermined period of time, HMD 802 may turn on light sources 806A to 806C to form light-source combination 804D. Further, the HMD 802 may repeat the above cycle of light-source combinations 804A to 804D one or more times.

ii. Analyzing the Video to Detect Controlled Glints

Since the timing of the sequence of light-source combinations is generally known, an HMD may know which glints to search when analyzing the video of the eye to detect controlled glints. More specifically, at block 706 of method 700, the HMD may analyze individual frames of the video for controlled glints captured in each frame. To do so, the HMD may first determine which light sources were switched on when the frame was recorded (e.g., by determining what combination in the sequence was formed when the frame was recorded). As such, the HMD can more efficiently analyze the frame by searching for just the controlled glints that correspond to the light sources that were switched on when the frame was recorded.

Figure 8B:
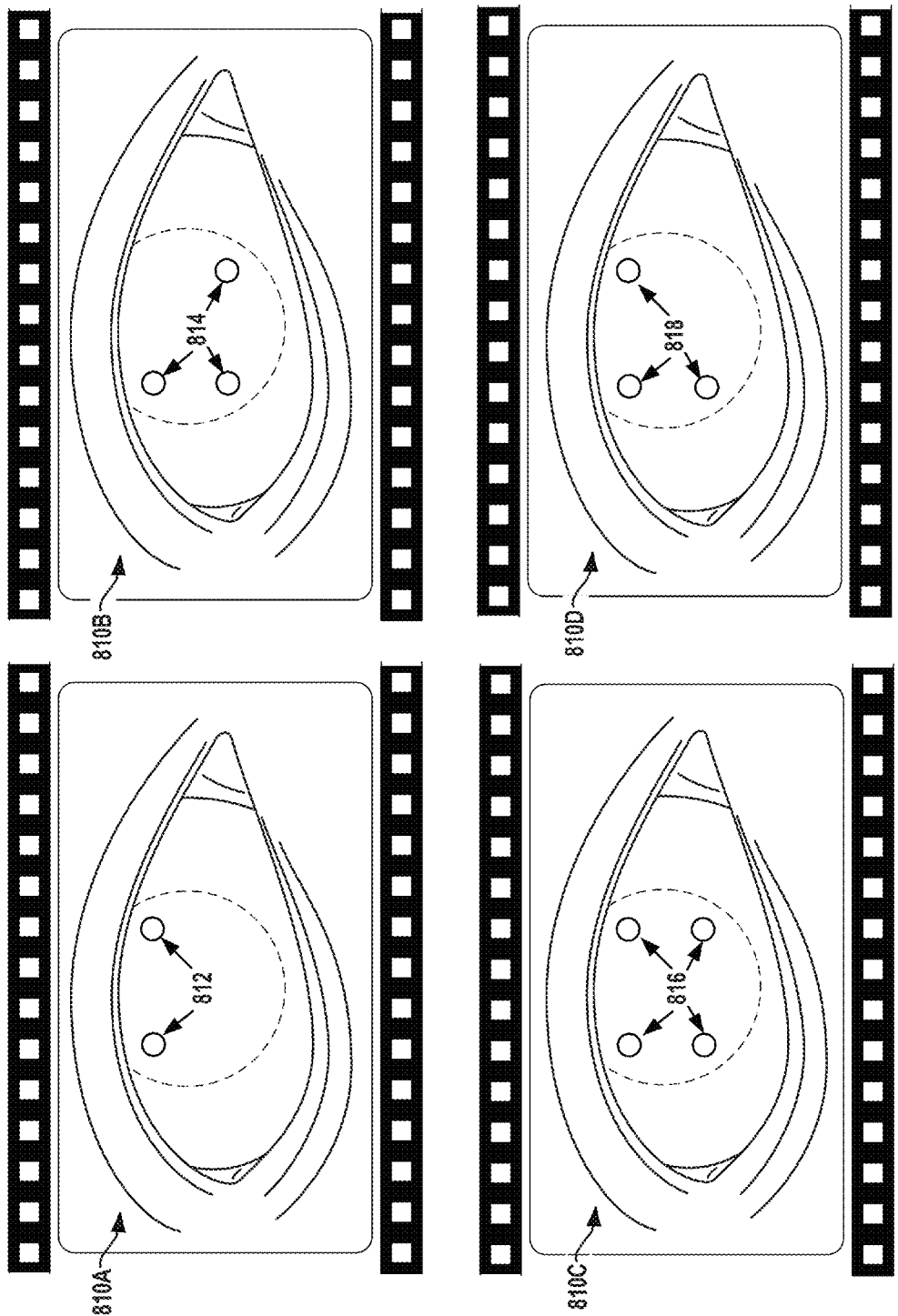
FIG. 8B is a simplified illustration of frames from a video of the eye that is captured during the sequence of light-source combinations shown in FIG. 8A, according to an exemplary embodiment.

FIG. 8B is a simplified illustration of frames from a video of the eye that is captured during the sequence of light-source combinations shown in FIG. 8A, according to an exemplary embodiment. In particular, frames 810A to 810D capture controlled the glints that correspond to light-source combinations 804A to 804D, respectively.

More specifically, frame 810A captures controlled glints 812 that correspond to light-source combination 804A (i.e., controlled glints that result from light sources 806A and 806B reflecting off the eye). Similarly, frame 810B captures controlled glints 814 that correspond to light-source combination 804B (i.e., controlled glints corresponding light sources 806A, 806C, and 806D), frame 810C captures controlled glints 816 that correspond to light-source combination 804C (i.e., controlled glints corresponding all light sources 806A to 806D), and frame 810D captures controlled glints 818 that correspond to light-source combination 804D (i.e., controlled glints corresponding light sources 806A to 806C).

Note that in some embodiments, light-sources forming one light-source combination in a sequence may be left on until it is time for the next light-source combination in the sequence. In such an embodiment, a light source that is switched on in consecutive light-source combinations in the predetermined sequence may simply be left on when the HMD switches from the first of the consecutive combinations to the second. For example, in such an embodiment, switching from light-source combination 804A to light-source combination 804B may involve switching off light source 806B, switching on light sources 806C and 806D, and simply leaving light source 806A switched on. Other examples are also possible.

In other embodiments, an HMD may turn off all light sources in between light-source combinations in the sequence. For example, the HMD may turn on the light sources for a given combination for a certain period of time and then turn off all the light sources for a certain period of time before turning on the light source that form the next combination in the sequence.

Note that the period for which each combination is formed and/or the period for which the HMD turns off all light sources between combinations in the sequence may vary, depending upon the particular implementation. For instance, in some implementations, the HMD 802 may flash light-source combinations such that each light-source combination is formed for a short period, with the light sources otherwise being turned off. By turning off the light sources in between combinations in the sequence, such an implementation may help to conserve power and/or may provide other benefits.

Further, in such an implementation, the timing with which the HMD flashes the light-source combinations may be substantially phase-synchronized with the frames of the video that is capturing the eye. For example, the light-source combinations may be flashed such that glints corresponding to the switched-on light sources are captured in each video frame. To do so, the sequence of light-source combinations may be timed according to the frame rate of the video, such that the HMD forms the next combination in the sequence before the next frame in the video of the eye is captured. Thus, for any two consecutive frames in the video of the eye, the light-source combination that is formed when the first of two consecutive frames is recorded will differ from the light-source combination that is formed when the second of the consecutive frames is recorded.

In some embodiments, the predetermined pattern with which the light sources are switched on and off may be such that no more than one light source is switched off in any given light-source combination. Since having more light sources generally results in having more controlled glints that can be used to determine eye position, increasing the number of switched on light sources when a given image of the eye is captured may improve the accuracy with which eye position can be measured based on the corresponding glints. Thus, a sequence of light-source combinations in which no more than one light source is switched off in any given combination, may facilitate more accurate eye tracking than a sequence that includes combinations with more than one light source switched off.

Figure 9:
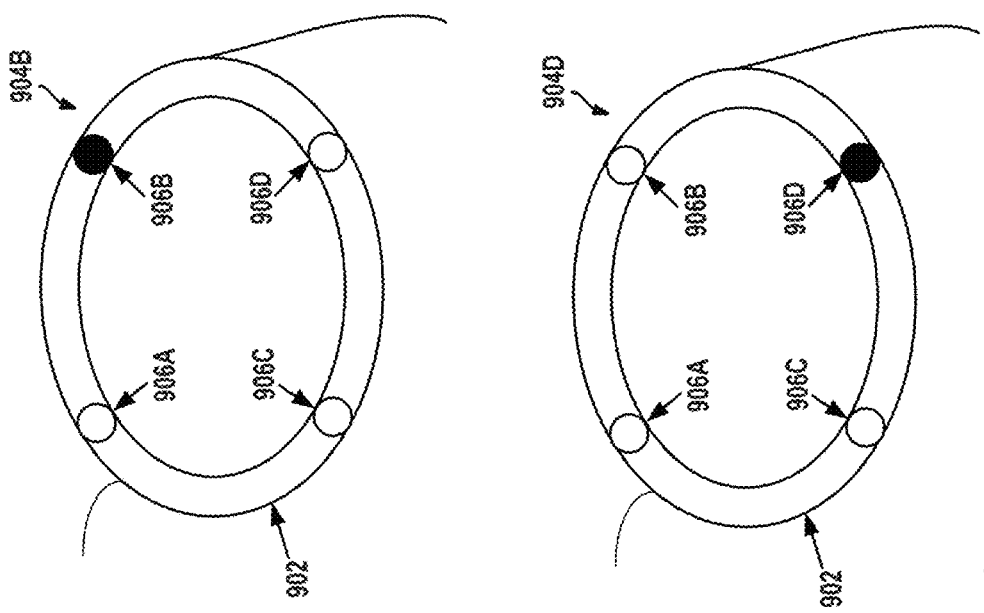
FIG. 9 is a simplified illustration of a predetermined sequence of light-source combinations, according to an exemplary embodiment.
Figure 9:
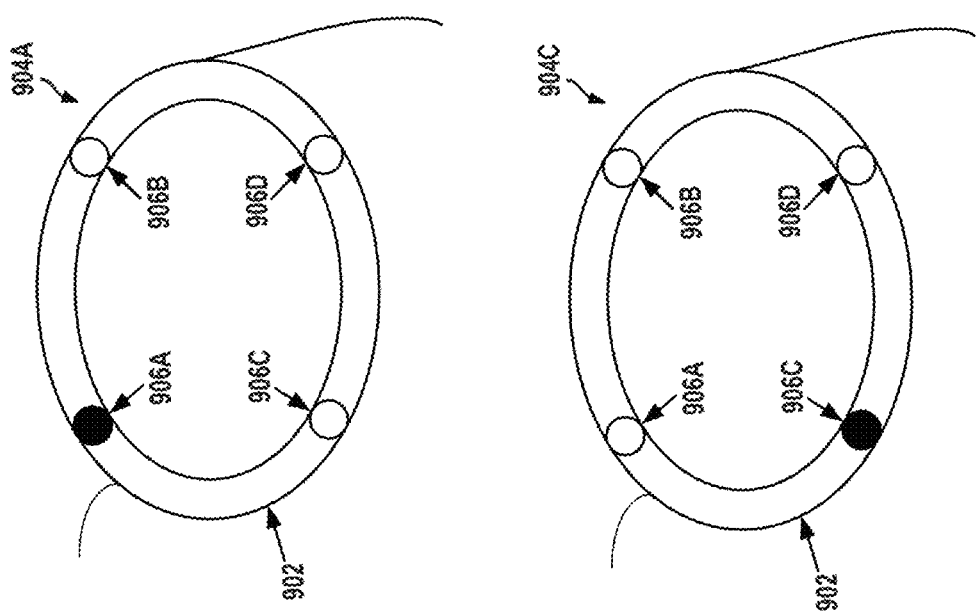

FIG. 9 is a simplified illustration of a predetermined sequence of light-source combinations, according to an exemplary embodiment. Specifically, FIG. 9 illustrates a sequence of light-source combinations 904A to 904D in which no more than one light source is switched off in any given combination. More specifically, in the first light-source combination 904A in the sequence, light source 906A is switched off, while light sources 906B, 906C, and 906D are switched on. In the second light-source combination 904B in the sequence, light source 906B is switched off, while light sources 906A, 906C, and 906D are switched on. In the third light-source combination 904C in the sequence, light source 906C is switched off, while light sources 906A, 906B, and 906D are switched on. Lastly, in the fourth light-source combination 904D in the sequence, light source 906D is switched off, while light sources 906A, 906B, and 906C are switched on.

It should be understood that the examples in FIGS. 8A, 8B, and 9 are provided for illustrative purposes, and that numerous variations on the illustrated examples and other examples are possible. For instance, while FIGS. 8A, 8B, and 9 illustrate an HMD with four light sources arranged in a rectangular relationship, the number of light sources and arrangement of light sources on the HMD may vary. Further, while FIGS. 8A, 8B, and 9 illustrate examples in which the predetermined pattern takes the form of a sequence of four light-source combinations, the number of light source combinations in such a sequence may vary, without departing from the scope of the invention. Other examples and variations on the above described examples are possible as well.

iii. Determining Eye Position Based on Controlled Glints

Referring back to blocks 706 and 708 FIG. 7, an HMD may use various techniques to determine a measure of eye position based on the detected glints. In particular, the HMD may determine an eye position on a frame by frame basis. Thus, as each frame is evaluated, the HMD may determine the eye position at the time the frame was recorded.

For example, at block 706 of method 700, the HMD may have determined which light sources were switched on when a given frame was recorded (e.g., the light-source combination corresponding to the frame) and, if analysis of the frame is successful, will have detected controlled glints that correspond to the particular light-source combination. As such, to determine eye position at block 708, the HMD may determine the spatial relationship between the controlled glints that are detected in a given frame, and then determine an eye position based on this spatial relationship.

In particular, the spatial relationship between controlled glints in a frame may vary depending upon the position of the eye. More specifically, since the light sources are generally fixed, but the curvature of the surface of the eye is such that the distance from the surface of the eye to a fixed light source will typically vary as the eye rotates within the orbit. Thus, the angle at which the light source reflects from the surface of the eye (e.g., from the cornea and/or sclera) may vary depending upon the position of the eye. Therefore, when multiple fixed light sources are directed towards the eye, the spatial relationship between the glints corresponding to the light sources may vary, depending upon the respective angles of reflection that result from the current eye position. More details of such a method (albeit without any variation in which light sources are switched on and off) are described in Hammoud, Passive Eye Monitoring, pp. 136-141, 202-204.

In a further aspect, by determining the eye position over the course of a video with multiple frames, the HMD may evaluate eye movement during the time when the video was recorded. For example, to determine eye movement, the HMD may determine the change in eye position over the two or more frames of the video. The HMD may then quantify the change in position by, e.g., determining an eye-movement value (e.g., an angular movement of the eye in the orbit) that corresponds to the change in eye position over the two or more frames of the video. Other examples are also possible.

It should be understood that while exemplary methods such as method 700 are described by way of example as being implemented by an HMD, an exemplary method may also be implemented in whole or in part by other types of computing devices. For example, an exemplary method may be implemented in whole or in part by a mobile phone, a tablet computer, a laptop or desktop computer equipped with a camera, and/or a network-enabled camera. Other examples of computing devices or combinations of computing devices that can implement an exemplary method are possible. In general, an exemplary method may be implemented by any computing device, system, or combinations of computing device(s) and/or system(s) that are configured to provide the same or similar functions as described herein.

As noted above, an exemplary method such as method 700 may also be carried out in whole or in part by a device or system, or by a combination of one or more devices and/or one or more systems, which are in communication with and can receive eye-tracking data from a device or system that captures the eye tracking data (e.g., an HMD). For example, an exemplary method may be implemented in whole or in part by a server system, which receives data from a device such as an HMD.

VI. CONCLUSION

The above detailed description describes various features and functions of the disclosed systems, devices, and methods with reference to the accompanying figures.

In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a computing system. Such a computing system may include various computing devices or components thereof, such as a processor or microprocessor for implementing specific logical functions or actions in the method or technique.

The program code and/or related data may be stored on any type of computer-readable medium, including non-transitory computer-readable media such as a storage device, including a disk drive, a hard drive, or other storage media. The computer-readable medium may include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

We claim:

1. A method comprising:
    receiving, by a computing system, infrared (IR) image data of an inner surface of a lens of a head-mountable device (HMD), wherein the image data is captured while the inner surface of the lens is illuminated with infrared light;
    detecting, by the computing system, in the IR image data of the inner surface of the lens, a reflection of an eye area on the inner surface of the lens;
    detecting, by the computing system, in the IR image data of the inner surface of the lens, a variable IR interaction pattern of the lens;
    determining, by the computing system, a lens that corresponds to the detected variable IR interaction pattern;
    calibrating, by the computing system, an eye-analysis process based on the determined lens; and
    after calibrating the eye-analysis process, applying the eye-analysis process to the reflection of the eye area to determine data corresponding to an eye.

2. The method of claim 1, wherein calibrating the eye-analysis process based on the determined lens comprises adjusting the eye-analysis process based on one or more characteristics of the determined lens.

3. The method of claim 1, wherein the one or more characteristics of the determined lens comprise one or more of: (a) pantoscopic tilt, (b) wrap, and (c) curvature radius.

4. The method of claim 1, wherein the variable IR interaction pattern of the lens is formed by a reflective coating on at least one surface of the lens.

5. The method of claim 4, wherein the reflective coating comprises an infrared-reflective coating that is selectively applied to form the Variable IR interaction pattern.

6. The method of claim 1, wherein an infrared-reflective coating is selectively applied to the lens to reflect IR light in a shape of a machine-readable code.

7. The method of claim 1, wherein an infrared-reflective coating is selectively applied to the lens to allow IR light to pass through a portion of the lens in a shape of a machine-readable code.

8. The method of claim 1, wherein the eye-analysis process comprises a process for determining position of the eye based at least in part on the reflection of the eye area from the inner surface of the lens.

9. The method of claim 1, wherein the eye-analysis process comprises a process for determining movement of the eye based at least in part on a plurality of reflections of the eye area from the inner surface of the lens, which are detected in a plurality of IR images of the eye area.

10. The method of claim 1, wherein the lens is a first lens, and wherein variable IR interaction pattern comprises a first machine-readable code, the method further comprising:
    detecting, in subsequent IR image data of the inner surface of the lens, a second machine-readable code resulting from an IR absorption pattern of the lens, wherein the second machine-readable code is different from the first machine-readable code; and
    in response to detecting the second machine-readable code that is different from the first machine-readable code:
        (i) determining a second lens that corresponds to the second machine-readable code; and
        (ii) recalibrating the eye-analysis process based on the second lens.

11. A head-mountable device (HMD) comprising:
    a lens comprising an variable infrared (IR) interaction pattern that corresponds to the lens;
    an IR light source arranged on a frame of the HMD to emit IR light towards the at least one lens;
    an IR camera arranged on a frame of the HMD and operable to capture IR image data while the at least one lens is illuminated by the IR light source;
    an onboard computing system that is operable to:
        detect, in the IR image data, a reflection of an eye area off of the inner surface of the lens;
        detect, in the IR image data, the variable IR interaction pattern on the lens;
        determine a lens that corresponds to the variable IR interaction pattern;
        calibrate an eye-analysis process based on the determined lens; and
        apply the calibrated eye-analysis process to the reflection off of the eye area to determine data corresponding to an eye.

12. The device of claim 11, wherein the HMD comprises a modular HMD.

13. The device of claim 12, wherein the modular HMD further comprises:

a frame component comprising the lens; and a housing component that comprises an attachment feature for attaching and detaching the frame from the housing.

14. The device of claim 13, wherein the control system is further operable to detect when the frame is initially attached and to responsively detect the variable IR interaction pattern of the lens, determine that the lens that corresponds to the detected machine-readable code, calibrate the eye-analysis process based on the determined lens, apply the calibrated eye-analysis process to determine data corresponding to the eye.

15. The device of claim 11, wherein the calibration of the eye-analysis process comprises one or more adjustments to the eye-analysis process based on one or more characteristics of the determined lens.

16. The device of claim 15, wherein the one or more characteristics of the determined lens comprise one or more of: (a) pantoscopic tilt, (b) wrap, and (c) curvature radius.

17. The device of claim 11, wherein the variable IR interaction pattern of the lens is formed by an infrared-reflective coating on at least one surface of the lens.

18. The device of claim 17, wherein the infrared-reflective coating is selectively applied to the lens in the shape of the machine-readable code.

19. The device of claim 17, wherein the infrared-reflective coating is selectively applied to the lens in an outline of a shape of the machine-readable code.

20. An optical lens comprising:

an inner surface having a variable infrared (IR) interaction pattern formed thereon by a selectively applied optical coating;

wherein the variable infrared (IR) interaction pattern defines a machine-readable code, and wherein the machine-readable code identifies the optical lens.

* * * * *